United States Patent
Lasters et al.

(10) Patent No.: US 7,702,465 B2
(45) Date of Patent: Apr. 20, 2010

(54) METHOD, COMPUTING ROUTINE, DEVICE FOR PREDICTING PROPERTIES OF MHC/PEPTIDE COMPLEXES, AND DATA AND PEPTIDES PRODUCED THEREFROM

(75) Inventors: Ignace Lasters, Antwerpen (BE); Johan Desmet, Kortrijk (BE)

(73) Assignee: Algonomics N.V., Zwijnaarde (BE)

( * ) Notice: Subject to any disclaimer, the term of this patent is extended or adjusted under 35 U.S.C. 154(b) by 1245 days.

(21) Appl. No.: 10/516,628

(22) PCT Filed: Jun. 10, 2003

(86) PCT No.: PCT/EP03/06049

§ 371 (c)(1),
(2), (4) Date: Sep. 7, 2005

(87) PCT Pub. No.: WO03/105058

PCT Pub. Date: Dec. 18, 2003

(65) Prior Publication Data

US 2006/0111554 A1 May 25, 2006

(30) Foreign Application Priority Data

Jun. 10, 2002 (EP) .................................. 02447115

(51) Int. Cl.
*G06F 19/00* (2006.01)
*C07K 14/74* (2006.01)
*C07K 14/435* (2006.01)

(52) U.S. Cl. ........................ 702/19; 702/27; 530/350; 435/7.1

(58) Field of Classification Search .................. None
See application file for complete search history.

(56) References Cited

U.S. PATENT DOCUMENTS 6,226,603 B1  1/2001  Luque et al.

FOREIGN PATENT DOCUMENTS

WO    WO 98/59244 A    12/1998

OTHER PUBLICATIONS

Rognan et al. J.Med. Chem-42(22).4650-4658,1999.*
Bohm et al. Journal of Computer-Aided Molecular Design, vol. 8, No. 3, p. 243-256, 1994.*

(Continued)

*Primary Examiner*—Michael Borin
(74) *Attorney, Agent, or Firm*—Amster, Rothstein, Ebenstein LLP

(57) ABSTRACT

The present invention relates to a method for structure-based prediction of properties of peptides and peptide analogs in complex with major histocompatibility (MHC) class I and class II molecules. The properties mainly relate to the three-dimensional structure of an MHC/peptide complex and the binding affinity of a peptide for an MHC receptor. The invention further relates to a computer program and a device therefor. The invention further relates to data produced by a method of the invention. The invention further relates to peptides and peptide analogs predicted to bind to target-MHC molecules. The present invention thus relates to the field of immunology, with possible applications in manufacture of vaccinates, de-immunization of proteins, and manufacture of therapeutic agents, especially immunotherapeutic agents.

17 Claims, 8 Drawing Sheets

OTHER PUBLICATIONS

Gohke et al. Current Opinion in Structural Biology, vol. 11, Issue 2, 2001, p. 231-235.*

Miyazawa et al. Proteins: Structure, Function, and Genetics, 1999, vol. 36, Issue 3, pp. 357-369.*

Marelius et al., "Sensitivity of an empirical affinity scoring function to changes in receptor-ligand complex conformations", European Journal of Pharmaceutical Sciences, vol. 14, No. 1, Aug. 2001, pp. 87-95.

Head et al., "Validate: A new method for the receptor-based prediction of binding affinities of novel ligands", Journal of the American Chemical Society, vol. 118, 1996, pp. 3959-3969.

Knegtel et al., "Molecular docking to ensembles of protein structures", Journal of Molecular Biology, vol. 266, No. 2, 1997, pp. 424-440.

Desjarlais et al., "Computer search algorithms in protein modification and design", Current Opinion in Structural Biology, vol. 8, No. 4, Aug. 1998, pp. 471-475.

* cited by examiner

METHOD, COMPUTING ROUTINE, DEVICE FOR PREDICTING PROPERTIES OF MHC/PEPTIDE COMPLEXES, AND DATA AND PEPTIDES PRODUCED THEREFROM

FIELD OF THE INVENTION

The present invention relates to a method for structure-based prediction of properties of peptides and peptide analogs in complex with major histocompatibility (MHC) class I and class II molecules. The said properties mainly relate to the three-dimensional structure of an MHC/peptide complex and the binding affinity of a peptide for an MHC receptor. The invention further relates to a computer program and a device therefor. The invention further relates to data produced by a method of the invention. The invention further relates to peptides and peptide analogs predicted to bind to target-MHC molecules. The present invention thus relates to the field of immunology, with possible applications in manufacture of vaccinates, de-immunization of proteins, and manufacture of therapeutic agents, especially immunotherapeutic agents.

BACKGROUND OF THE INVENTION

Cytotoxic T-cells ($T_C$ or CD8-T lymphocytes) and helper T-cells ($T_H$ or CD4-T lymphocytes) have the capability of recognizing short, processed fragments of a protein antigen, referred to as antigenic peptides or T-cell epitopes. However, recognition does not occur by direct binding to free peptides. Specific receptor molecules on T-cells (T-cell receptors or TCRs) recognize a peptide antigen only when it is bound to another receptor known as a major histocompatibility complex (MHC) molecule. Such MHC-peptide complexes serve the role of cell markers: when the MHC contains an endogenous (self) peptide, it marks the cell as "healthy"; when it contains a foreign peptide, the cell is marked as "infected". The MHC-mediated presentation of antigenic peptides to the repertoire of T-cells can thus be seen as the primary stimulus to elicit an immune response. Depending on the type of MHC presenting an antigen, which is correlated with the type of cell expressing it, the immune system is triggered to either destroy the antigen presenting cell or to produce antibodies directed against the infectious agent.

MHC molecules are subdivided into classes I and II. While their general function is the same (presenting antigen), they differ in a number of aspects. MHC class I is expressed on the cell surface as a heterodimeric complex between a 46-kDa heavy chain (the a-chain) and a 12 kDa light chain (the β2-microglobulin or β2m chain). The α-chain consists of three domains, $\alpha_1$, $\alpha_2$ and $\alpha_3$; the $\alpha_1$ and $\alpha_2$ domains are responsible for binding of a peptide ligand, while the $\alpha_3$ domain is membrane-bound and involved in CD8 co-receptor binding. Class II MHC molecules have the same overall shape, although they are constituted of two membrane-bound chains: an α chain of ~35 kDa and a β chain of ~28 kDa. Both the α and the β chain form two domains ($\alpha_1$ and $\alpha_2$ on the one hand and $\beta_1$ and $\beta_2$ on the other). The $\alpha_1$ and $\beta_1$ domain jointly form the peptide binding domain. The $\beta_2$ domain is involved in CD4 co-receptor binding.

Both MHC class I and class II molecules show a high degree of polymorphism. They have been further subdivided into different subtypes. The existence of different MHC allotypes lies at the basis of the capacity of MHCs to bind a broad range of peptides while still preserving some specificity. Given this polymorphism, being able to predict which peptides specifically bind to which MHC subtypes, is thought to be of great value in vaccination strategies and de-immunization programs. Thanks to the recent burst of information derived from experimentally determined 3D-structures, valuable insights about the determinants of peptide binding specificity have been obtained. This, in turn, has led to the idea that a structure-based prediction of potentially antigenic peptides (or T-cell epitopes) is within reach.

Functional human leukocyte antigens (HLAs or human MHCs) are characterized by a deep binding groove to which endogenous as well as potentially antigenic peptides bind. The groove is further characterized by a well-defined shape and physico-chemical properties. HLA class I binding sites are closed, in that the peptide termini are pinned down into the ends of the groove. They are also involved in a network of hydrogen bonds with conserved HLA residues (Madden, D. R. et al., (1992) Cell 70, 1035-1048). In view of these restraints, the length of bound peptides is limited to 8-10 residues. Superposition of the structures of different HLA complexes confirmed a general mode of binding wherein peptides adopt a relatively linear, extended conformation. At the same time, a significant variability in the conformation of different peptides was observed also. This variability ranges from minor structural differences to notably different binding modes. Such variation is not unexpected in view of the fact that class I molecules can bind thousands of different peptides, varying in length (8-10 residues) and in amino acid sequence. The different class I allotypes bind peptides sharing one or two conserved amino acid residues at specific positions. These residues are referred to as anchor residues and are accommodated in complementary pockets (Falk, K. et al., (1991) Nature 351, 290-296). Besides primary anchors, there are also secondary anchor residues occupied in more shallow pockets (Matsumura, M. et al., (1992) Science 257, 927-934). In total, six allele-specific pockets termed A-F have been characterized (Saper, M. A. et al., (1991) J. Mol. Biol. 219, 277-312; Latron, F. et al., (1992) Science 257, 964-967). The constitution of these pockets varies in accordance with the polymorphism of class I molecules, giving rise to both a high degree of specificity (limited cross reactivity) while preserving a broad binding capacity.

In contrast to HLA class I binding sites, class II sites are open at both ends. This allows peptides to extend from the actual region of binding, thereby "hanging out" at both ends (Brown. J. et al., (1993) Nature 364, 33-39). Class II HLAs can therefore bind peptide ligands of variable length, ranging from 9 to more than 25 amino acid residues. Similar to HLA class I, the affinity of a class II ligand is determined by a "constant" and a "variable" component. The constant part again results from a network of hydrogen bonds formed between conserved residues in the HLA class II groove and the main-chain of a bound peptide. However, this hydrogen bond pattern is not confined to the N- and C-terminal residues of the peptide but distributed over the whole of the chain. The latter is important because it restricts the conformation of complexed peptides to a strictly linear mode of binding. This is common for all class II allotypes. The second component determining the binding affinity of a peptide is variable due to certain positions of polymorphism within class II binding sites. Different allotypes form different complementary pockets within the groove, thereby accounting for subtype-dependent selection of peptides, or specificity. Importantly, the constraints on the amino acid residues held within class II pockets are in general "softer" than for class I. There is much more cross reactivity of peptides among different HLA class II allotypes. Unlike for class I, it has been impossible to identify highly conserved residue patterns in peptide ligands (so-called motifs) that correlate with the class II allotypes.

The different characteristics of class I and class II MHC molecules are responsible for specific problems associated with the prediction of potential T-cell epitopes. As discussed before, class I molecules bind short peptides that exhibit well-defined residue type patterns. This has led to various prediction methods that are based on experimentally determined statistical preferences for particular residue types at specific positions in the peptide. Although these methods work relatively well, uncertainties associated with non-conserved positions limit their accuracy. Prediction methods for MHC class II-mediated T-cell epitopes essentially follow the same strategy, but are hampered by the fact that the binding groove is open. The latter makes it difficult to locate, in a pool of peptides identified as binders, the 9-residue segment that is actually responsible for the binding. This fact, combined with the intrinsically weaker constraints of the complementary pockets in class II binding grooves, makes the establishment of (pseudo-) motifs very difficult (Mallios, R. R. (2001) *Bioinformatics* 17, 942-948). On the other hand, class II peptide binding motifs generally include more anchor residues than class I motifs.

Methods for MHC/peptide binding prediction can grossly be subdivided into two categories: "statistical methods" that are driven by experimentally obtained affinity data and "structure-related methods" that are based on available 3D structural information of MHC molecules.

Statistical methods have been promoted under the impulse of a growing amount of binding data. Sources of binding information are, typically, elution and pool sequencing of peptides bound naturally to MHC molecules inside cells (Falk, K. et al., (1994) *Immunogenetics* 39, 230-242), phage display of peptide libraries (Hammer, J. et al., (1993) *Cell* 74, 197-203. Fleckenstein, B. et al., (1999) *Sem. Immunol.* 11, 405-416), data sets compiled from reports in the literature (Brusic, V. et al., (1998) *Nucleic Acids Res.* 26, 368-371, Rammensee, H. G. et al., (1999) *Immunogenetics* 50, 213-219). A common approach is to decompose, in a statistical way, the available experimental information into MHC type-specific and peptide residue position-specific numerical values reflecting the preference for individual amino acid types at that position (Parker, K. C. et al., (1994) *J. Immunol.* 152, 163-175). The matrices obtained in this way may then serve as profiles from which the binding affinity of a peptide sequence of interest can be estimated.

Structure-based methods generally include a first step wherein the structure of a specific MHC/peptide complex is modeled and a second step wherein the binding strength of the peptide is estimated from the modeled complex in accordance with an empirical scoring function. Examples include WO 98/59244, Altuvia, Y. et al., (1995) *J. Mol. Biol.* 249, 244-250; Doytchinova, I. A. and Flower, D. R. (2001) *J. Med. Chem.* 44, 3572-3581). Alternatively, a molecular dynamics simulation is sometimes performed to model a peptide within an MHC binding groove (Lim, J. S. et al. (1996) *Mol. Immunol.* 33, 221-230). Another approach is to combine loop modeling with simulated annealing (Rognan, D. et al., (1999) *J. Med. Chem.* 42, 4650-4658). Most research groups emphasize the importance of the scoring function used in the affinity prediction step. Schueler-Furman et al. (Schueler-Furman, O. et al., (2000) *Prot. Sci.* 9, 1838-1864) apply a statistical potential to evaluate the contacts between the peptide and the MHC receptor. Rognan et al. (1999) rely on a quantification of physicochemical effects (like H-bond formation, lipophilic contacts, desolvation, etc.). Swain et al. (Swain, M. T., et al., (2001) *Proceedings of the second IEEE International Symposium on Bioinformatics and Biomedical Engineering.* IEEE computer Society Press, Bethesda, Md., pp. 81-88) also apply a heuristic scoring function based on inter-atomic contacts, electrostatic interactions and H-bond formation. Doytchinova and Flower (2001) consider essentially the same contributions but follow a quantitative structure-affinity relationship (QSAR) method to assess the binding affinity. Logean et al. (Logean, A., et al., (2001) *Bioinorg. & Med. Chem. Letters* 11, 675-679) have analyzed the performance of 7 universal scoring functions. They found that many of these scoring functions yield poor correlation with experiment, in contrast to their "Fresno" scoring function. However, it was also recognized that the Fresno function cannot be universally applied but requires recalibration for different protein-ligand systems.

There is a need to substantially improve both the structure prediction and the affinity assessment steps of methods which predict the affinity of a peptide for a major histocompatibility (MHC) class I or class II molecule. The main problem encountered in this field is the poor performance of prediction algorithms with respect to MHC alleles for which experimentally determined data (both binding and structural information) are scarce. It is an aim of the present invention to provide a novel method for predicting the affinity of a peptide for a major histocompatibility (MHC) class I or class II molecule, also in cases where experimental information is rare.

SUMMARY OF THE INVENTION

The present invention relates to a method for predicting the binding affinity of a peptide for a major histocompatibility (MHC) class I or class II molecule, comprising the following steps:

(a) receiving a representation of a complete or partial three-dimensional structure of an MHC class I or class II molecule, (b) obtaining an ensemble of representations of peptide backbone structures of said peptide, said representations located within the binding site of said MHC molecule, (c) modeling for each peptide backbone structure of said ensemble in relation to said MHC molecule, at least the side-chains of said peptide, thereby obtaining an ensemble of modeled MHC/peptide complexes, and (d) evaluating the binding properties of said peptide for said MHC molecule, comprising at least:

(d1) evaluating one or more components of the potential energy of each complex of the ensemble of step (c).

(d2) evaluating the conformational entropy for the complete ensemble of step.

An accurate and efficient method is provided which uses a three-dimensional structure to predict the binding affinity of an MHC molecule/peptide complex. It fulfills a need for obtaining structural and physicochemical data on peptide MHC complexes, without the requirement for laboratory equipment, space, expertise and time. Furthermore, it provides the means to screen large numbers of potentially antigenic peptides and further provides the means for creating a database which may be examined for trends or which may be used as the basis for other experiments.

A step which obtains an ensemble of backbone structures and a separate step which models the side-chains offer the advantages of sampling more efficiently the conformational space of the backbone, reducing the computational time required to model the side-chains, and provides a more accurate overall model of the complex(es).

Combining potential energy and conformational entropy in the evaluation step leads to an improved accuracy in the prediction of the binding affinity. The present inventors have observed the surprising improvement in the correlation between experimentally-determined and predicted binding affinities when both components are explicitly computed.

In one embodiment of the present invention the said representation of step (a) is obtained from one of the following:
- one or more experimentally determined structures obtained by, for example, X-ray crystallography, nuclear magnetic resonance spectroscopy, scanning microscopy, or,
- one or more models derived from one or more experimentally determined structures, whereby said experimentally determined structures have a high sequence identity to said MHC molecule.

The option to use experimentally-determined structures leads to a more accurate prediction of the affinity of the complex since the said structures have been experimentally validated and may have a higher degree of accuracy. The option to use computer-modeled structures may allow the prediction of affinities of peptide for MHC molecules in complexes for which no or only partial MHC molecule structures exist. Since more MHC molecules are known than structures have been experimentally solved, the use of modeled structures allows the prediction of otherwise unobtainable complex affinity data, filling the growing need for such information.

In another embodiment of the present invention the ensemble of step (b) is generated by a computer modeling method, said method being able to generate multiple energetically favorable backbone configurations in relation to the MHC molecule. The use of modeling to generate said ensemble allows the available conformational space to be sampled efficiently, for example in a fashion that is specific for the sequence of said peptide. This provides validation for allowable conformations, and may also provide a more accurate assessment of properties of the complex.

In another embodiment of the present invention the representation of step (b) is retrieved from a library of peptide structures pre-oriented in relation to the MHC molecule. The use of a library provides the opportunity of a drastic reduction of the computational time per peptide since an alternative is to use simulations which may be extremely demanding in computing time due to the large search space. An indirect advantage is the fact that the prediction accuracy can be improved because a large number of pre-oriented peptide structures may be retrieved, and more attention can be paid to the important side-chain placement and affinity prediction steps.

In yet another embodiment of the present invention a complex within said ensemble of step (c) is obtained from a side-chain placement algorithm. The use of a side placement algorithm decouples the side-chain from the main-chain sampling so providing an opportunity to increase the speed and accuracy of the calculation.

In yet another embodiment of the present invention the side-chain placement of step (c) not only involves placing the side-chains of the peptide itself, but also involves placing one or more side-chains of said MHC molecule that are in contact with said peptide. The use of both a side-chain placement for peptide and MHC molecules provides the opportunity to generate more accurate models and hence to increase the accuracy of the predicted affinity of the complex.

In yet another embodiment of the present invention a complex within said ensemble of step (c) is obtained from a side-chain placement algorithm suited for global side-chain optimization. The globally optimal placement of side-chains generally yields more accurate predictions compared to local optimization.

In yet another embodiment of the present invention the side-chain placement algorithm of a method above comprises a dead-end elimination (DEE) algorithm, characterized in that said DEE algorithm eliminates rotameric conformations on the basis of a mathematical criterion that allows the detection of conformations that are not compatible with the globally optimal conformation. The DEE approach is helpful in solving the combinatorial search problem by reducing the number of possible rotamers which need to be tested, thereby greatly increasing the speed of global side-chain optimization.

In yet another embodiment of the present invention the side-chain placement algorithm of a method above comprises a FASTER algorithm (Desmet J. et al. (2002) *Proteins* 48, 31-43), said algorithm being characterized essentially by a repeated perturbation, relaxation and evaluation step. The FASTER algorithm improves the side-chain prediction accuracy at a low computational cost, and hence makes provision for more accurate predictions of binding affinity.

In yet another embodiment of the present invention the binding affinity of step (d) of a method above is represented by a single scoring value for the whole ensemble of MHC/peptide complexes, said scoring value comprising the sum of the conformational entropy for the complete ensemble of MHC/peptide complexes, and the average of the said energetical components of each of the complexes of said ensemble. Conformational entropy is a fundamental property of a complex that is preferably computed from an ensemble of structures. The explicit inclusion of conformational entropy contributes in a favorable way to the correlation between predicted and experimental affinities. Furthermore, the incorporation of significant energetic components, in combination with an entropical component, allows a more accurate assessment of the affinity of the complex.

In yet another embodiment of the present invention the binding properties of step (d) of a method above are evaluated for the global complex, thereby accounting for interactions between pairs of residues from the peptide, the MHC molecule and both the peptide and the MHC molecule. The use of global scoring which accounts for interactions between said pairs of residues provides a more accurate assessment of the global energy of the system and hence provides a more exact measure of the affinity of the complex.

In yet another embodiment of the present invention the entropical component of a method above reflects the overall conformational flexibility of the peptide. Conformational flexibility is a fundamental property of complexes that is non-trivial to simulate or quantify. Furthermore, the simulation and quantification of conformational flexibility may provide useful insights.

In yet another embodiment of the present invention the representations of said peptide contained in said library of a method above are derived from experimentally determined structures. The presence of experimentally-determined structures in the library provides the option to use structures which have been experimentally validated. Said structures may have a higher degree of accuracy and consequently lead to a more accurate prediction of the affinity of the complex.

In yet another embodiment of the present invention the representations of said peptide contained in said library of a method above are derived from computer-generated structures, said structures generated by said computer modeling method described above. The presence of computer-modeled structures in the library may allow the prediction of peptide affinities for MHC molecules in complexes for which no or only partial structural information is available. Since only few complex structures have been experimentally solved, the use of modeled structures allows structure-based affinity prediction for complexes of unknown structure, filling the growing need for such information.

In yet another embodiment of the present invention said peptide of a method above comprises one or more non-naturally occurring amino acids. The use of non-naturally occurring amino acids provides the possibility for obtaining affinity data for compounds in which the feature provides additional properties, for example a therapeutic property, increased in vivo stability, increased intrinsic activity, reduced toxicity.

In yet another embodiment the invention relates to a method for producing an immunogenic peptide comprising an MHC class I or class II restricted T cell epitope that binds to an MHC class I or class II molecule and induces an MHC class I or II-restricted cytotoxic T cell response, said method comprising steps of:

(a) providing an amino acid sequence of a polypeptide of interest;

(b) preparing one or more overlapping putative immunogenic peptide fragments of said polypeptide of interest, for instance consisting of 8 to 20 amino acids;

(c) receiving a representation of a complete or partial three-dimensional structure of said MHC class I or class II molecule, (d) obtaining an ensemble of representations of peptide backbone structures of said putative immunogenic peptides, said representations located within the binding site of said MHC molecule, (e) modeling for said peptide backbone structures of said ensemble in relation to said MHC molecule, at least the side-chains of said putative immunogenic peptide, thereby obtaining an ensemble of modeled MHC/peptide complexes, (f) evaluating the binding properties of said putative immunogenic peptides for said MHC molecule, comprising at least:

f1) evaluating one or more components of the potential energy of each complex of the ensemble, f2) evaluating the conformational entropy for the complete ensemble of each MHC/peptide complex, (g) inferring from the results obtained in (f), one or more putative immunogenic peptides that bind to said MHC molecule, (h) optionally preparing one or more of said putative immunogenic peptides of said polypeptide of interest, (i) optionally testing complexes of said one or more putative immunogenic peptides said MHC molecule for an ability to be recognized by a MHC cytotoxic T cells, and to thereby induce a cytotoxic T cell response to the epitope, and (e) (optionally) selecting said one or more putative immunogenic fragments comprising an MHC class I or class II binding site that induce an MHC class I or class II cytotoxic T cell response to the epitope.

In a preferred embodiment, the one or more overlapping putative immunogenic peptide fragments of said polypeptide of interest consist of 5, 6, 7, 8, 9, 10, 11, 12, 13, 14, 15, 16, 17, 18, 19, 20, 21, 22, 23, 24, 25 or more amino acids.

In a further embodiment of the present invention said representation of step (c) is obtained from one of the following:

one or more experimentally determined structures obtained by for example X-ray crystallography, nuclear magnetic resonance spectroscopy, scanning microscopy, or one or more models derived from an experimentally determined structure, whereby said experimentally determined structure has a high sequence identity to said MHC molecule.

In a further embodiment of the present invention said representation of step (d) is generated by a computer modeling method, said method being able to generate multiple energetically favorable backbone configurations in relation to said MHC molecule.

In a further embodiment of the present invention said representation of step (d) is retrieved from a library of peptide structures pre-oriented in relation to said MHC molecule.

In a still further embodiment of the present invention a complex within said ensemble of step (e) is obtained from a side-chain placement algorithm.

In a further embodiment of the present invention the side-chain placement of step (e) not only involves placing the side-chains of the peptide itself, but also involves placing at least one side-chain of said MHC molecule that are in contact with said peptide.

In another embodiment of the present invention a complex within said ensemble of step (e) is obtained from a side-chain placement algorithm suited for global side-chain optimization.

In a further embodiment of the present invention the side-chain placement algorithm is a dead-end elimination (DEE) algorithm, characterized in that said DEE algorithm eliminates rotameric conformations on the basis of a mathematical criterion that allows the detection of conformations that are not compatible with the globally optimal conformation.

In a further embodiment of the present invention the side-chain placement algorithm is a FASTER algorithm, said algorithm being characterized by a repeated perturbation, relaxation and evaluation step.

In a further embodiment of the present invention the binding affinity of step (f) is represented by a single scoring value for the whole ensemble of MHC/peptide complexes, said scoring value comprising the sum of the conformational entropy for the complete ensemble of MHC/peptide complexes, and the average of the said energetical components of each of the complexes of said ensemble.

In a further embodiment of the invention the binding affinity of step (f) is evaluated for the global complex, thereby accounting for interactions between pairs of residues from the peptide, the MHC molecule and both the peptide and the MHC molecule.

In a further embodiment of the invention the entropical component reflects the overall conformational flexibility of the peptide.

In a further embodiment of the invention wherein the representations of said peptide contained in said library are derived from experimentally determined structures.

In a further embodiment of the present invention the representations of said peptide contained in said library are derived from computer-generated structures, said structures generated by said computer modeling method of claim 18.

In a still further embodiment of the present invention said peptide comprises one or more non-naturally occurring amino acids.

In yet another embodiment the present invention relates to any method herein described wherein said MHC class I molecule comprises an HLA antigen selected from any of the HLA-A, HLA-B, HLA-C, HLA-E, HLA-F and HLA-G genes or gene products or a gene product from any of the alleles of these genes.

In yet another embodiment the present invention relates to any method herein described wherein said MHC class II molecule comprises an HLA antigen selected from any of the HLA-DR, HLA-DQ and HLA-DP genes gene products or a gene product from any of the alleles of these genes. Some non-limiting examples HLA alleles can be found for instance on the following web address: http://www.anthonynolan.com/HIG/lists/class1list.html.

A further embodiment of the present invention is data comprising:
  representations of one or more peptide backbone structures, each peptide demonstrating an interaction with an MHC class I or class II molecule, and
  an indication of the MHC molecule associated with said representation.

Data comprising information about MHC molecules, peptides, and complexes of both provide a source for data-mining, of, for example, therapeutically useful peptides. Structural information, represented as data, obviates the need to model said structures using methods known in the art, so providing a significant time- and hence cost-saving.

A further embodiment of the present invention is a computer program comprising computing routines, stored on a computer readable medium for evaluating the binding affinity of a peptide for an MHC class I or class II molecule, said routines comprising:
  receiving an ensemble of representations of structures of the complex between said MHC molecule and said peptide,
  evaluating the potential energy of each complex of the ensemble,
  evaluating the conformational entropy for the complete ensemble.

A computer routine for evaluating the binding affinity of a peptide for an MHC molecule provides the advantage of speed and allows for the integration with other routines. By integrating the routine, the possibility exists, for example, for automation, efficient transfer of data and the provision of tools for the interpretation of data.

Another embodiment of the present invention is a computer program as described above, further comprising modeling for each peptide backbone structure of said ensemble in relation to said MHC molecule, at least the side-chains of said peptide.

Another embodiment of the present invention is a computer program as described above, wherein said peptide backbone structures are obtained by computer modeling or by retrieval from a database.

An embodiment of the present invention is a device for evaluating the binding affinity of a peptide for an MHC class I or class II molecule, comprising:
  receiving an ensemble of representations of structures of the complex between said MHC molecule and said peptide,
  evaluating the potential energy of each complex of the ensemble,
  evaluating the conformational entropy for the complete ensemble.

A device which performs a method of the present invention, alleviates the user from the task of performing the said method, so offering a time- and cost-saving.

A further embodiment of the present invention is an (unknown) peptide which binds MHC class I or class II molecules, said peptide being obtainable by using a method above.

A further embodiment of the present invention is an (unknown) peptide which binds MHC class I or class II molecules, said peptide being obtained by using a method above.

Another embodiment of the present invention is a nucleic acid (capable of) encoding a peptide as defined above.

Another embodiment of the present invention is a nucleic acid of at least 15 nucleotides in length (capable of) specifically hybridizing with the nucleic acid as defined above.

Another embodiment of the present invention is an antibody specifically recognizing a peptide as defined above.

Yet another embodiment of the present invention is an antibody specifically recognizing a nucleic acid as defined above.

Yet another embodiment of the present invention is a method for producing a peptide as defined above comprising:
  (i) culturing host cells comprising a nucleic acid according as defined above, under conditions allowing the expression of the peptide, and,
  (ii) recovering the produced peptide from the culture.

Yet another embodiment of the present invention is a peptide as defined above for use as a medicament.

Yet another embodiment of the present invention is a nucleic acid as defined above for use as a medicament.

DETAILED DESCRIPTION OF THE INVENTION

The present invention relates to a method for structure-based prediction of the affinity of potentially antigenic peptides for major histocompatibility (MHC) receptors. More specifically, a method to provide a quantitative assessment of the affinity of a selected peptide sequence for a selected MHC allotype through (i) analysis of the three-dimensional structure of an MHC peptide binding domain, (ii) by generating multiple conformations for the backbone of the selected peptide, (iii) by optimizing the side-chain conformation for each MHC/peptide main-chain structure, and (iv) by computing the expected binding affinity of the MHC/peptide complex, thereby including a conformational entropy component derived from the set of generated conformations. The application of this method to multiple peptides and/or multiple MHC receptor types may be helpful to identify the most antigenic peptides originating from a common source, for example from a specific viral or bacterial species or a therapeutic protein molecule. This, in turn, may be useful in vaccination or de-immunization applications.

In one embodiment of the present invention, a first step comprises receiving an experimentally determined three-dimensional (3D) structure for a selected MHC class I or class II allotype is retrieved. If a suitable 3D structure is not available, it is modeled by homology to a known structure which preferably has a maximal amino acid sequence identity with the selected MHC allotype. The retrieved or modeled structure consists, at least, of those amino acid residues forming the peptide binding site.

In a second step, multiple conformations for the main-chain of the selected peptide are generated, either by retrieval from an MHC/peptide main-chain library or by a suitable computer modeling algorithm, preferably a docking algorithm. The said library may be a compilation of experimentally determined structures or structures generated in advance by a suitable computer modeling algorithm, preferably a docking algorithm.

In a third step, for each peptide main-chain conformation generated in the second step, the conformation of side-chains of the selected peptide are modeled by applying a suitable side-chain placement algorithm, preferably a FASTER or a DEE method, in conjunction with a first energy-based scoring function, preferably a potential or free energy function. The co-modeling of the MHC receptor structure with that of the peptide is a preferred option. The result of this third step is a set of full complex structures at atomic level of detail.

In a fourth step, the ensemble of modeled structures obtained in the third step is evaluated in accordance with a second scoring function hereinafter called the "affinity scoring function". The latter is suited especially to evaluate the binding affinity of a peptide ligand to a receptor. The affinity scoring function preferably includes components related to the conformational energy, the effect of solvent, and parametrized amino acid type-based terms. An essential component of the affinity function is the incorporation of an entropical contribution, preferably derived in accordance with statistical mechanical laws and applied to the complete ensemble of modeled structures, as generated in the third step. The explicit generation of structural ensembles is intended to account for, essentially, the conformational freedom (or flexibility, microstates, entropy etc.) of the complex.

A method of the present invention concerns the quantitative prediction of the binding affinity of a given peptide for a given MHC allotype. A method might be applied to multiple peptides and/or multiple receptors by repeated application of the basic method for a single peptide/receptor system.

In one embodiment of the invention, the considered MHC molecules are of any class, preferably of class I and class II.

In another embodiment of the present invention, there are no limitations to the amino acid composition or the length of the simulated peptide. In another embodiment, the length of each simulated class I-binding peptides is less than 30 residues, preferably less than 20 and more preferably between 8 to 10 residues. In another embodiment, the length of class II simulated peptides is less than 30 residues, preferably less than 20 and more preferably restricted to nonapeptides (9-residue peptides) in view of the experimental evidence that fragments of this length form the region of contact with the receptor binding groove.

A method of the present invention relates to the quantitative prediction of affinity values. Properties that are directly related with binding affinity comprise binding free energy, association/dissociation constants and $IC_{50}$ values. The prediction of these values also forms part of the invention. Properties that are indirectly related with binding affinity comprise, for example, association/dissociation rates (on/off rates), immunogenicity and conformational flexibility. An aspect of the present invention may be a method for prediction of kinetic and immunogenic properties. Another aspect of the present invention may be a method for simulation and quantification of conformational flexibility.

A method of the present invention provides a novel approach to structure-based prediction of MHC/peptide affinities, comprising a quantitative assessment of the affinity of a selected peptide sequence for a selected MHC allotype through four computational steps.

The first three steps relate to the prediction of multiple 3D structures for the selected MHC/peptide complex by gradually adding levels of detail in the consecutive modeling steps. The fourth step analyzes structural information and applies a specific scoring function in order to translate the structural information into a predicted peptide binding affinity. A method of the present invention comprises steps 1 to 4, summarized as follows (see also FIG. 1).

1. MHC template construction. A suitable 3D model for the selected MHC allotype is generated, either by retrieval from the Protein Databank (PDB) or by a standard homology modeling method. This model serves as an input template structure for the next steps. The model is devoid of any peptide structure, i.e. the binding groove is "emptied". For the purpose of this section only, the model is referred to as "MHC".

2. MHC/peptide main-chain construction. The MHC template structure from step 1 is complemented with an ensemble of peptide backbone (i.e. main-chain) conformations. This leads to an ensemble of 3D structures consisting of a structurally constant part, MHC, and a variety of peptide main-chain structures. For the purpose of this section only, the said ensemble is named "$\{p_{mc}\}$". The union of MHC and the multiple representations of peptide backbones is denoted as "$\{MHC/p_{mc}\}$" in this description. The latter set of structures may be generated, for example, by a suitable computer modeling algorithm that yields multiple energetically feasible peptide backbone configurations in relation to MHC, called, for the purpose of this description, a "docking approach". In another example, the set of structures may be generated by a method which retrieves pre-oriented peptide structures from a library, said method called the "database approach" for the purpose of this description. Both approaches are discussed in detail below.

3. MHC/full peptide construction. A third step concerns the addition and modeling of side-chains. In accordance with the amino acid sequence of the selected peptide, each residue position of $p_{mc}$ in each structure of the set $\{MHC/p_{mc}\}$ is provided with the correct side-chain. In the event that the correct side-chains are already present (for example, if step 2 was performed by docking of the same peptide), the mutation step may be skipped. More important is the modeling of each $MHC/p_{mc}$. In one embodiment of the present invention, this is accomplished by a suitable side-chain placement algorithm such as a FASTER or a DEE method. The modeling of side-chains may not necessarily be limited to those of the peptide; one aspect of the invention is to include in this step a number MHC side-chains as well. Even if step 2 was performed by a docking method, the invention allows for the remodeling of at least all receptor side-chains in contact with the peptide, in addition to the side-chains of the peptide itself. Thus, step 3 of a method of the present invention delivers an ensemble of full complex structures at atomic detail, denoted as $\{MHC/p_{full}\}$ for the purposes of this description, wherein the side-chain conformations are optimally adapted to each $p_{mc}$ structure in relation to MHC.

4. MHC/peptide affinity assessment. One aim of step 4 is to compute a single scoring value reflecting the binding affinity of the selected peptide for the selected MHC allotype. A source of input data is the structural information obtained in step 3. The final score of the considered system is obtained by applying a function called the affinity scoring function, F, for the purpose of the present description, which has been optimized so as to correlate with the true thermodynamic free energy of binding. As explained further below, this function comprises preferably components related to the conformational energy, the effect of the solvent, and specific amino acid type-based terms that have been parametrized. These types of contributions are not ensemble properties, i.e. they are computed for each individual structure of the set $\{MHC/p_{full}\}$. Yet, working with multiple structures, or ensembles, enables certain structure-derived contributions to be averaged, thereby reducing the noise level. Processing these contributions leads to a first component of the predicted affinity under the form of an average energy component for the whole ensemble, termed <E> for the purpose of the present description. Another essential component of F is the entropical contribution (termed S for the purpose of the present invention), derived in accordance with statistical mechanical rules and accounted for by an equation:

$$F = <E> - c\,S \qquad [1]$$

In equation [1], c is a parametrized constant which theoretically corresponds with the absolute temperature (in degrees Kelvin) at which the MHC/peptide system is simulated. The entropy contribution S is preferably taken to be the logarithm of the number of energetically acceptable structures within the set $\{MHC/p_{full}\}$. Clearly, S is an ensemble property reflecting the overall conformational flexibility of the selected peptide in the complex. It is also noteworthy that the more negative <E> and the more positive S, the lower will be F, thus the higher will be the predicted affinity, in agreement with thermodynamic principles.

In step 2 of the invention—obtaining an ensemble of multiple conformations for the main-chain of the peptide located in the target-MHC binding site—two means for generating said ensembles are suggested as examples:

(A) A basic method, also referred to as the "docking approach", wherein peptide main-chain conformations or "binding modes" are generated via molecular modeling, preferably peptide docking.

(B) An advanced method, also referred to as the "database method", wherein peptide main-chain conformations are retrieved from a database of structures.

An underlying hypothesis of the database method might be explained by the following: peptides can assume only a limited number of binding modes, irrespective of their amino acid sequence. Assuming the validity of this hypothesis, this means that different independently performed docking experiments of peptides varying in sequence (but not in length) are likely to show some partial overlap between the generated ensembles. In a more formal notation this corresponds to the situation wherein—

$$\{MHC/p_{mc}\} \cap \{MHC/p'_{mc}\} \neq \emptyset \quad [2]$$

The merging of a sufficient number of ensembles resulting from independent docking experiments with different peptide sequences may therefore lead to the establishing of a generalized ensemble of possible $MHC/p_{mc}$ structures, hereby denoted as $\{MHC/P_{mc}\}$. The exact amino acid sequence of each peptide in this ensemble then becomes irrelevant (in view of the structural overlap between the constituting populations). In other words, the set $\{MHC/P_{mc}\}$ might be seen as the structure MHC provided with a variety of pure peptide backbone conformations, or "poly-alanine" peptide conformations.

An aspect of the present invention in which peptide main-chain conformations are retrieved from a library has advantages over other methods. One advantage is of course a drastic reduction of the computational time per peptide. Docking simulations are often extremely demanding in computing time because of the huge search space. (The latter consists of three translational, three rotational and a large number of conformational degrees of freedom, making up a total space with very high dimension.) An indirect advantage is the fact that the prediction accuracy can be improved because more attention can be paid to the important side-chain placement and affinity prediction steps. Finally, for various technical reasons some peptide binding modes may be missed in a docking experiment, whereas they are de facto represented in the generalized ensemble, on condition that the latter covers the full accessible space.

An ensemble $\{MHC/P_{mc}\}$ only depends on two variables: MHC allotype and peptide length. Any sequence information may be suppressed in view of the scope of any such ensemble: representing peptide main-chain binding modes. In one embodiment of the present invention, $MHC/P_{mc}$ structures are preferably stored in a format wherein the peptides are converted into poly-alanine fragments. In another embodiment, a generic database may be compiled from different MHC allotype-specific and peptide length-specific structural libraries.

Such a database may be used, for example, to predict affinities for peptides of different length or to predict the affinity of a given peptide for different MHC types.

Detailed steps of a method of the present invention comprise the following:

1. Construction of an MHC template. A method of the present invention requires two basic elements of input data, besides a number of execution parameters (see FIG. 2 for a schematic overview of the complete method). The first element is the selection of an MHC allotype of interest, the second one is the sequence of a peptide as present in a protein source of interest, for example a viral protein. Selecting an MHC allotype is equivalent to selecting the amino acid sequence representing the MHC allele. With this sequence (or a reference to it) it is possible to search the protein data bank (PDB) for the presence of 3D structures sharing the same amino acid sequence. If such structure exists, it can be retrieved from the PDB (Berman, H. M. et al., (2000) *Nucleic Acids Res.* 28, 235-242) and used as a three-dimensional MHC template structure in the further prediction steps. In the event that more than one candidate structure is available, the user has to decide which one is the most preferred starting structure. Useful criteria for this purpose are the crystallographic resolution and refinement, the absence of missing atoms, and/or the criteria applied by structure validation tools such as the Biotech Validation Suite (www.embl-heidelberg.de, and follow links therein for the Biotech Validation Suite).

In the case that neither the PDB database nor available publications describe the structural co-ordinates of a sequence identical to that of the selected MHC allotype, a template structure may be constructed by homology modeling. Various methods for homology modeling include, for example Swiss-Model (Guex, N. and Peitsch, M. C. (1997) *Electrophoresis* 18, 2714-2723, 1997) or SCWRL (Bower, M. et al., (1997) *J. Mol. Biol* 267, 1268-1282). Because the modeling of MHC binding grooves involves no insertions or deletions, a pure side-chain placement algorithm can be applied. A preferred method to accomplish this is a DEE method (De Maeyer et al., 2000) or the FASTER method as described by Desmet et al. (Desmet, J. et al., (2002) *Proteins* 48, 31-43). Once a template structure has been retrieved or modeled, it is within the scope of the present invention to refine it by performing 100-200 steps of steepest descent energy minimization, or by any equivalent energy minimization procedure. Such energy minimization action is a standard procedure in protein modeling and serves to solve potential atomic conflicts or suboptimal positioning.

In one embodiment of the invention, a method which is followed by a user in advanced execution mode i.e. the database approach, merely involves the selection of the appropriate $\{MHC/P_{mc}\}$ ensemble from the database, said ensemble corresponding with the MHC allotype of interest. In this case the MHC template construction step may not be explicitly executed but is implicitly present in the structure retrieved from the database.

2. MHC/peptide main-chain construction. One step of the present method is the construction of an ensemble of peptide main-chain configurations $\{p_{mc}\}$ in relation to the MHC template, or $\{MHC/p_{mc}\}$. The selected peptide p is characterized by a well-defined amino acid sequence. It is logical to assume that the sequence of p has at least some influence on the ensemble of binding modes or, in other words, that $\{MHC/P_{mc}\}$ is sequence-specific. On the other hand, the very nature of MHC class I and class II binding grooves also suggests that the number of distinct binding modes is limited. Therefore, the construction of peptide backbones might be performed in more than one way. For example a sequence-specific {MHC/$p_{mc}$} ensemble is created for each new peptide. Or in another example a generalized ensemble {MHC/$P_{mc}$} might be made available, representing at least the conformational space of the selected peptide p. An over-representation of the space is not so much of a problem because the generalized ensemble {MHC/$P_{mc}$} may be reduced to the peptide-specific ensemble {MHC/$p_{mc}$} in step 3 of a method wherein MHC-incompatible binding modes are identified after side-chain placement. Furthermore, the establishing of a generalized ensemble can be accomplished in a straightforward manner by unifying different peptide-specific ensembles until a sufficient overlap between the populations is observed. Consequently, step 2 of a method of the present invention reduces to the problem of generating peptide-specific {MHC/$p_{mc}$} ensembles.

An example of a method of constructing the peptide backbone is found in Desmet et al. (1997, 2000). This docking method is a combinatorial algorithm for flexible docking of peptides to the binding site on a protein receptor molecule in which the peptide is constructed from scratch in relation to the chosen receptor structure, thereby avoiding any potential bias from a starting structure of the receptor/peptide complex. It yields a collection of different, energetically favorable complex structures wherein the peptide assumes, typically, between 0 and 500 distinct binding states. This de novo peptide building method is therefore the most preferred approach to generate the contemplated {MHC/$p_{mc}$} ensembles. The method of Desmet et al. (1997, 2000) is herein explicitly incorporated by reference. Its essential execution steps and characteristics are outlined in the following.

The docking method referred to above consists of a combinatorial buildup algorithm that "grows" the peptide by gradual addition of a single residue adopting a specific main-chain conformation. For each residue type there are 47 low energy main-chain rotamers and for each main-chain rotamer there are a variable number of backbone-compatible side-chain rotamers. Glycine, proline and N- or C-terminal residues form an exception and have 125, 35 and 12 main-chain rotamers, respectively. The rotamer library thus represents the entire conformational space for each residue type.

The docking algorithm starts from a peptide fragment of length one, i.e. a user-selected root residue. (This can be any residue of the peptide.) The accessible space for the root residue is searched by a combined translational, rotational and conformational exploration. Translations and rotations are performed in a discretized fashion in accordance with a grid approach. The conformational sampling is done separately for the main-chain and side-chain parts of the system. The main-chain conformation is only varied for the peptide, whereas that of the receptor is strictly kept fixed. Possible main-chain conformations for the peptide, in this case the root residue, are selected from the main-chain rotamer library (containing mostly 47 rotamers per residue type). Possible side-chain conformations are retrieved from a backbone-dependent side-chain rotamer library. Besides the side-chain of the peptide's root residue, up to about 40 side-chains from the receptor can be modeled simultaneously. The side-chain placement step is fully repeated for every translational-rotational-(backbone)-rotameric combination of the root residue, one such step called a single docking step. The side-chain placement itself is performed by a standard DEE method (Desmet et al., 1992). The net result of each docking step is an energetical value, $E_{bind}$, reflecting the "quality of fit" of the peptide's root residue in the considered binding mode. $E_{bind}$ is computed by a rich function, including the interaction energy between the peptide (root) fragment and the receptor, the total fragment self-energy and the augmentation of the receptor self-energy due to conformational changes induced by the presence of the fragment. This value serves as a discriminator between energetically acceptable and prohibited binding modes (applying a user-defined threshold value). All energetically acceptable single-residue fragments are added to a peptide fragment repository.

The buildup of the peptide continues by combining each previously accepted fragment in the repository with the available main-chain rotamers of an adjacent residue. Each new combination is again processed individually by the DEE-based side-chain placement algorithm. All energetically favorable fragments are added to the peptide fragment repository. This buildup process continues until all residues of the peptide have been extended to their full length. Thus, in the end the peptide fragment repository contains only energetically acceptable full-length peptides.

One aspect of a fragment repository is that it may hold only information related to the binding mode of the peptide's main-chain; reference to a specific conformation for the side-chains may not be stored.

One embodiment of the present invention is the storage of modes identified by the docking method into a general database of {MHC/$P_{mc}$} ensembles. In view of the usage of such database in providing a generic source of binding modes (i.e. when applying the advanced database-related operation mode of a method of the present invention), the peptide conformations are preferably stored as poly-alanine or poly-glycine constructs. The only form of specificity in the database concerns the MHC allotype and length of the generic peptide fragments.

3. MHC/full peptide construction Step 3 of a method of the present invention involves the reconstruction of peptide and optionally the receptor side-chain conformations in order to build full complex structures. This structural information forms the main source of input information for the next step 4 of the present method.

In view of the fact that the present invention is almost exclusively based on properties derived from predicted structures, the accuracy of this step is directly related to the prediction accuracy of the peptide binding affinity, i.e. an important aim of the present invention.

The accuracy of any side-chain placement method may be determined by three aspects: (i) the search method that is used to determine the optimal global side-chain arrangement, (ii) the rotamer library from where potential side-chain conformations are retrieved, and (iii) the quality of the scoring function used during conformational search. A fourth determinant of accuracy, i.e. the coupling between main-chain and side-chain conformational changes, is also considered. It may be implicitly calculated from the above because side-chain conformations are generated for a broad ensemble of peptide main-chain structures. The first three determinants of prediction accuracy are discussed in more detail.

1. Preferred side-chain conformational search method. The present inventors have recently developed a novel method for fast and accurate side-chain modeling called the "fast and accurate side-chain topology and energy refinement method" or FASTER method (Desmet et al., 2002). In view of its characteristics, the FASTER method is highly preferred to perform step 3 of the present method. The main reason for this is that FASTER allows a rapid yet accurate search for the globally optimal side-chain arrangement, which is one of the key-aspects of the present invention. More specifically, for each MHC/$P_{mc}$ structure of the ensemble generated in step 2, all side-chains of the peptide and a significant number of side-chains from the MHC receptor (typically 10-30) are modeled simultaneously in order to find the globally best packing arrangement. In doing so, all possible pair-wise interactions between two flexibly treated side-chains are taken into account during the modeling. This is in contrast to other methods (e.g. Swain et al., 2001) which only score the side-chain conformations of the peptide and which independently do this for each side-chain.

Apart from the FASTER method, other side-chain placement methods are suitable for performing step 3 of the present invention, such as DEE (De Maeyer et al., 2000), self-consistent mean field optimization (Koehl, P. and Delarue, M. (1994), *J. Mol. Biol.* 239, 249-275), simulated annealing (Shenkin, P. S. et al., (1996) *Proteins* 26, 323-352), a genetic algorithm (Tufféry, P. et al., (1997) *Protein Eng.* 10, 361-372) or Monte Carlo simulation (Holm, L. and Sander, C. (1992) *Proteins* 14, 213-223). In general, methods which explicitly account for pair-wise side-chain/side-chain interactions are preferred. Such methods may follow either a rotameric or a non-rotameric strategy.

2. Rotamer library. When performing step 3 on basis of the FASTER or a DEE method, the algorithm requires access to a library of discrete, preferential side-chain conformations or rotamers. Such library may be called a rotamer library. Non-limiting examples include Ponder and Richards (Ponder, J. W. and Richards, F. M. (1987) *J. Mol. Biol.* 193, 775-791), Tufféry et al. (Tufféry, P. et al., (1991). *J. Biomol. Struct. Dynam.* 8, 1267-1289), Holm and Sander, (1992); Schrauber et al., (Schrauber, H. et al., (1993) *J. Mol. Biol.* 230, 592-612), Dunbrack and Karplus, (Dunbrack, R. L. Jr. and Karplus, M. (1993) *J. Mol. Biol.* 230, 543-574), De Maeyer et al., 1997, Mendes et al. (Mendes, J. et al. (1999) *Proteins* 37, 530-543), Xiang and Honig, (Xiang, Z. and Honig, B. (2001) *J. Mol. Biol.* 311, 421-430). One way to define rotamers is to store them as a list of torsional angle values for all rotatable bonds within a particular side-chain type and for the chemical bond that connects it to the backbone. Alternatively, rotamers in the library may be stored as sets of atomic co-ordinates in a given reference frame. Whatever rotameric representation is chosen, it is preferred that the rotamer library provide the necessary and sufficient information to reconstruct side-chain conformations in an unambiguous way onto a polypeptide backbone. One example of a preferred rotamer library is the one devised by Mendes et al. (1999), comprising so-called "flexible rotamers". Herein, a flexible rotamer is essentially defined as an ensemble of sub-rotamers deviating slightly in structure from a classic rigid rotamer. The latter type of rotamers is especially suited for the present method since it enables quantification of side-chain entropical effects, both for peptide and receptor side-chains, in a similar fashion as for the peptide main-chain. Also preferred are highly detailed libraries of classic rigid rotamers, whether backbone-dependent (Dunbrack & Karplus, 1993; Bower et al., 1997, Desmet et al., 1997) or backbone-independent (De Maeyer et al., 1997; Xiang & Honig, 2001). A less preferred method for assigning side-chain conformations is by applying a non-rotameric approach such as a molecular mechanics or dynamics method, or a combination protocol (Rognan et al., 1999). Non-rotameric methods are preferred less because they are slower and less efficient in conformational sampling (Mendes et al., 1999), though they fall within the scope of the present invention.

3. Scoring function for side-chain placement. A method of the present invention distinguishes between two separate scoring functions, the first being applied to structure prediction of side-chains (and also peptide main-chains, if step 2 of the present method is performed by way of docking), and the second scoring function being applied in the affinity prediction step (see step 4. MHC/Peptide Affinity Assessment). As it is intended for usage in conjunction with a method for searching (sampling) huge conformational hyperspaces, the first scoring function is preferably intrinsically rapid to evaluate and, also, it does not have to include as many energetical components as an affinity scoring function. One purpose of the said scoring function is to allow the determination of the correct conformation of a specific MHC/peptide complex. For this reason, a standard potential or free energy function might be applied that accounts for the intramolecular interactions. Such a function is usually called a force field function. Non-limiting examples of widely used force fields include the CHARMM force field (Brooks, B. R. et al., (1983) *J. Comput. Chem.* 4, 187-217), the AMBER force field of Kollman and co-workers at UCSF (Weiner, S. J. et al., (1984) *J. Am. Chem. Soc.* 106, 765-784) and the DREIDING field (Mayo, S. L. et al., (1990) *J. Phys. Chem.* 94, 8897-8909). The applied energy function may include as many relevant energetic contributions as possible, non-limiting examples of which include van der Waals interactions, H-bond formation, electrostatic interactions and contributions related to chemical bonds (bond stretching, angle bending, torsions, planarity deviations). The present inventors have shown that these energy terms suffice to reach the currently highest possible accuracy in side-chain prediction while allowing very rapid modeling (Desmet et al., 2002). The scope of the present invention allows for force fields which satisfy any of the above. In one embodiment of the present invention, the preferred force field is CHARMM (Brooks et al., 1983).

4. MHC/peptide affinity assessment. The ligand binding affinity. ($K_b$) is related to the binding free energy ($\Delta G$) by the following equation.

$$\Delta G = -RT \ln(K_b) \quad [3]$$

where R is the ideal gas constant (8.31 J mol$^{-1}$ K$^{-1}$) and T the absolute temperature in degrees Kelvin. Further, $K_b$ is the inverse of the dissociation constant ($K_d$) which is approximately equal to the often mentioned IC$_{50}$ value.

$$\Delta G = RT \ln(K_d) \approx RT \ln(IC_{50}) \quad [4]$$

The binding free energy, $\Delta G$, is the difference in Gibbs free energy between the free receptor molecule plus the free peptide ligand on the one hand and the receptor/ligand complex on the other hand. Strongly negative $\Delta G$ values indicate strong binding. Differences in $\Delta G$ for different peptides and/or different MHC subtypes may be due to a variety of reasons, including enthalpic and entropic effects related to any of the free or bound states. Since many of these effects can by no means be deduced from theoretical simulations, affinity scoring functions might include more than one parametrized components. A basic approach of the present invention is then to incorporate into the predicted binding free energy, $\Delta G_{pred}$, as much relevant structural information as possible, and to cover all other effects by empirical components. Assuming that the different contributions are independent and additive, the following is an example of a general expression which reflects the predicted binding free energy:

$$\Delta G_{pred} = \sum_{i=1}^{N_S} s_i S_i + \sum_{i=1}^{N_P} p_i P_i \quad [5]$$

In equation [5], $S_i$ and $P_i$ are structure-derived and non-structure derived contributions, respectively. $N_S$ and $N_P$ are the number of considered contributions of both types while $s_i$ and $p_i$ are their respective weight coefficients. It should be noted, however, that most methods consider either structure-based or non-structure based terms but seldomly both. The coefficients $s_i$ and the number of structural components $N_s$ are in fact parameters as well since they need to be calibrated. The coefficients $p_i$ are in many methods set equal to unity.

With respect to the structure-related terms in Eq. [5], one approach is to sum over all contributions provided by a force field function (e.g. electrostatic, van der Waals, H-bonding terms, etc.). However, pure standard force field terms generally do not yield an optimal correlation with experimental data. Including additional effects, non-limiting examples of which include desolvation, freezing of rotatable bonds, special hydrophobicity terms, may significantly enhance correlation. The "Fresno" method (Rognan et al., 1999) considers five individual contributions: H-bonding, lipophilic contacts, rotatable bond freezing, burial of polar atoms and desolvation. This scoring function requires re-calibration of the weight coefficients for different MHC subtypes. The method of Schueler-Furman et al. (2000) only considers MHC side-chain/peptide side-chain contacts (with a special treatment of MHC side-chains in contact with the peptide backbone) in conjunction with a statistical pairwise potential.

Scoring functions based on experimental data often rely on the frequency of amino acid types observed at each position in a population of peptides (e.g. self peptides) that are known to bind to a specific MHC allele (Rammensee et al., 1999). Alternatively, the contribution of individual amino acid types at each position in a peptide sequence to the peptide's total binding affinity may be estimated by a number of statistical analyses. This can be done for a set of known binding peptides (Parker et al., 1994) or experimentally constructed peptides (Hammer et al., 1993; Fleckenstein et al., 1999).

A method of the present invention is predominantly based on 3D structural contributions. Structural contributions preferably comprise: (i) all terms that can be computed, using a force field e.g. CHARMM (Brooks et al., 1983), for a MHC/$P_{full}$ complex resulting from step 3 of a method; (ii) contributions computed in the same way for separately modeled reference states of the free peptide and receptor; (iii) contributions accounting for desolvation of both the receptor and the peptide upon complex formation, and (iv) importantly, entropical contributions derived in accordance with a statistical mechanical analysis of the ensemble of structures obtained in step 3, i.e. $\{MHC/P_{full}\}$.

When following the standard docking approach to generate the latter ensemble, one generally obtains a limited set of complex structures that are all energetically relaxed. In one embodiment of a method of the present invention, the contributions (i) to (iii) are added up for each structure of the ensemble and each sum is given the weight coefficient $s_i=1/(N_{sol})$, where $N_{sol}$ is the number of solutions in the ensemble. This yields the energetical term $<E>$ in Eq. [1]. The structure-related component (iv), corresponding to the entropical contribution S in Eq. [1], may be set equal to $\ln(N_{sol})$, or $k_B \ln(N_{sol})$ where $k_B$ is Boltzmann's constant. The latter constant may be included in the weight coefficient (c in Eq. [1], corresponding to $s_{entropy}$ in Eq. [5]). This coefficient is subject of global parameter optimization, which is to be executed by a suitable parameter optimization method. A non-limiting example illustrating the importance of including an entropical component is provided in EXAMPLE 4.

When a method of the present invention is performed in accordance with the advanced database-related execution mode, a more sophisticated method may be needed to determine the appropriate weight coefficients of aforementioned contributions (i) to (iv), preferably on the basis of statistical mechanical relationships.

Besides structure-related contributions ($S_i$ in Eq. [5]), it is within the scope of the present method to consider a number of non-structural terms ($P_i$ in Eq. [5]). A first possibility is a combination method formed by fusing a structure-based and an experimental method. This is accomplished by determining the globally optimal set of weight coefficients $\{s_i,p_i\}$, applying a suitable parameter optimization method.

A preferred possibility is to include topology contributions, for example the "Type and Topology Specific" (TTS) contributions of Desmet et al. (International Patent Application No. WO 02/05146) which has been invented in the context of protein design. This method considers a limited number of topology classes (typically 2 or 3), depending on a residue's degree of burial in a complex. The notion topology may also be extended so as to reflect, besides shielding from solvent, the chemical nature of a residue's environment, for example a measure of polarity. Furthermore, it is within the scope of the present invention to consider an alternative to the residue type dimension in the concept of TTS parameters, namely distinguishing chemical groups instead of residue types. A preferred classification of chemical groups is the following: 1, $CH_x$ aliphatic; 2, $CH_x$ aromatic; 3, $NH_x$ aromatic; 4, OH; 5, S+SH; 6, $NH_3^+$; 7, $COO^-$; 8, $CONH_2$; 9, $NHC(NH_2)_2^+$. This way, the type-dimension in the set of TTS parameters can be restricted to 9 groups (instead of 20 residue types). The option to work with chemical groups is fully compatible with the broader definition of topology. This creates a landscape of possibilities that can be explored by applying a suitable data mining and parameter optimization strategy, which is within the scope of the present invention. It is further within the scope of the invention to identify and quantify the most relevant contributions in the attempt to enhance the correlation between predicted and experimental $\Delta G$ values. The incorporation of type and topology-specific contributions again leads to a fully structure-based method.

As used herein, a "peptide" refers to at least two covalently attached amino acids which includes polypeptides and oligopeptides. The peptide may be made up of naturally occurring amino acids and peptide bonds, or non-naturally-occurring amino acids or synthetic peptidomimetic structures, i.e., "analogs" such as peptoids [see Simon, R. J. et al., (1992) Proc. Natl. Acad. Sci. U.S.A. 89(20), 9367-9371], generally depending on the method of synthesis.

The peptides of the invention can be prepared by classical chemical synthesis. The synthesis can be carried out in homogeneous solution or in solid phase. For instance, the synthesis technique in homogeneous solution which can be used is the one described by Houbenweyl in the book entitled "Methode der organischen chemie" (Method of organic chemistry) edited by E. Wunsh, vol. 15-I et II. THIEME, Stuttgart 1974. The peptides of the invention can also be prepared in solid phase according to the methods described by Atherton and Shepard in their book entitled "Solid phase peptide synthesis" (IRL Press, Oxford, 1989). The peptides according to this invention can be prepared by means of recombinant DNA techniques as described by Sambrook et al., Molecular Cloning: A Laboratory Manual 2nd edition, New York, Cold Spring Harbor Laboratory, 1989).

"Amino acid", or "residue", as used herein means both naturally occurring and synthetic amino acids. For example, homo-phenylalanine, citrulline, and norleucine are considered amino acids for the purposes of the invention. "Amino acid" also includes imino acid residues such as proline and hydroxyproline. In addition, any amino acid representing a component of the variant proteins of the present invention can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes.

In the preferred embodiment, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218:U138-U138 Part 2 Aug. 22, 1999, both of which are expressly incorporated by reference herein.

Aromatic amino acids may be replaced with D- or L-naphylalanine, DM or L-phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl) alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1-C20.

Acidic amino acids can be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —SO$_3$H) threonine, serine, or tyrosine.

Other substitutions may include unnatural hyroxylated amino acids may made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Alkyl includes heteroalkyl, with atoms of nitrogen, oxygen and sulfur. Preferred alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the variant polypeptides can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant polypeptides of to the present invention may include the following: Cysteinyl residues may be reacted with alpha-haloacetates (and corresponding amine), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, P-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5 to 7.0 because this agent is relatively specific for the histidyl side chain, and para-bromophenacyl bromide may also be used, e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues.

Other suitable reagents for derivatizing alpha-amino-containing residues include compounds such as imidoesters e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosyl residues per se is well-known, such as for introducing spectral labels into tyrosyl residues by reaction with aromatic diazonium compounds or tetranitromethane.

N-acetylimidizol and tetranitromethane may be used to form O-acetyl tyrosyl species and 3-nitro derivatives, respectively. Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

As used herein "side-chain placement algorithm" refers to methods for optimizing the side-chain conformations of residues. Non-limiting examples of such methods include International Patent Application No. WO 01/33438, De Maeyer et al (De Maeyer et al., (2000) *Methods in Molecular Biology*, vol. 143: *Protein Structure Prediction: Methods and Protocols.* Webster, D. (Ed.) Humana Press Inc., Totowa, N.J., pp. 265-304), Koehl, P. and Delarue, M. (*J. Mol. Biol.* (1994) 239, 249-275), Shenkin, P. S. et al., (Shenkin, P. S. et al., (1996) *Proteins* 26, 323-352), Tufféry et al. (Tufféry, P. et al., (1997) *Protein Eng.* 10, 361-372), Holm and Sander (*Proteins* (1992) 14, 213-223 1992). Further included are methods which explicitly account for pair-wise side-chain/side-chain interactions.

As used herein, "dead-end-elimination" or "DEE" refers to methods for testing which side-chain conformations are energetically incompatible with the globally optimal side-chain arrangement onto a protein backbone (or template) structure (e.g. Desmet, J. et al., (1992) *Nature* 356, 539-542). In a protein system to be tested, each amino acid residue is first represented by a limited set of discrete side-chain conformations obtained from a library of theoretically possible conformations, also known as a rotamer library. To arrive at a globally optimal conformation for the protein system, rotamers are screened in accordance to one or more mathematical expressions, called DEE criteria. Different valid elimination criteria have been identified in the past (De Maeyer, M., Desmet, J. and Lasters, I. (2000) The dead-end elimination theorem: mathematical aspects, implementation, optimizations, evaluation and performance. in: *Methods in Molecular Biology, vol.* 143: De Maeyer, M., Desmet, J. and Lasters, I. (2000) and references therein). Upon convergence, all but one rotamers have been eliminated for each modeled side-chain so that the final, unique assignment of rotamers corresponds to the global optimum. If convergence cannot be reached by merely applying DEE criteria, some additional end-stage routines are required (Desmet et al., 1997).

As used herein "fast and accurate side-chain topology and energy refinement" or "FASTER" refers to methods of International Patent Application No. WO 01/33438 which is incorporated herein by reference.

EXAMPLES

Example 1

Peptide Docking

Figure 1:
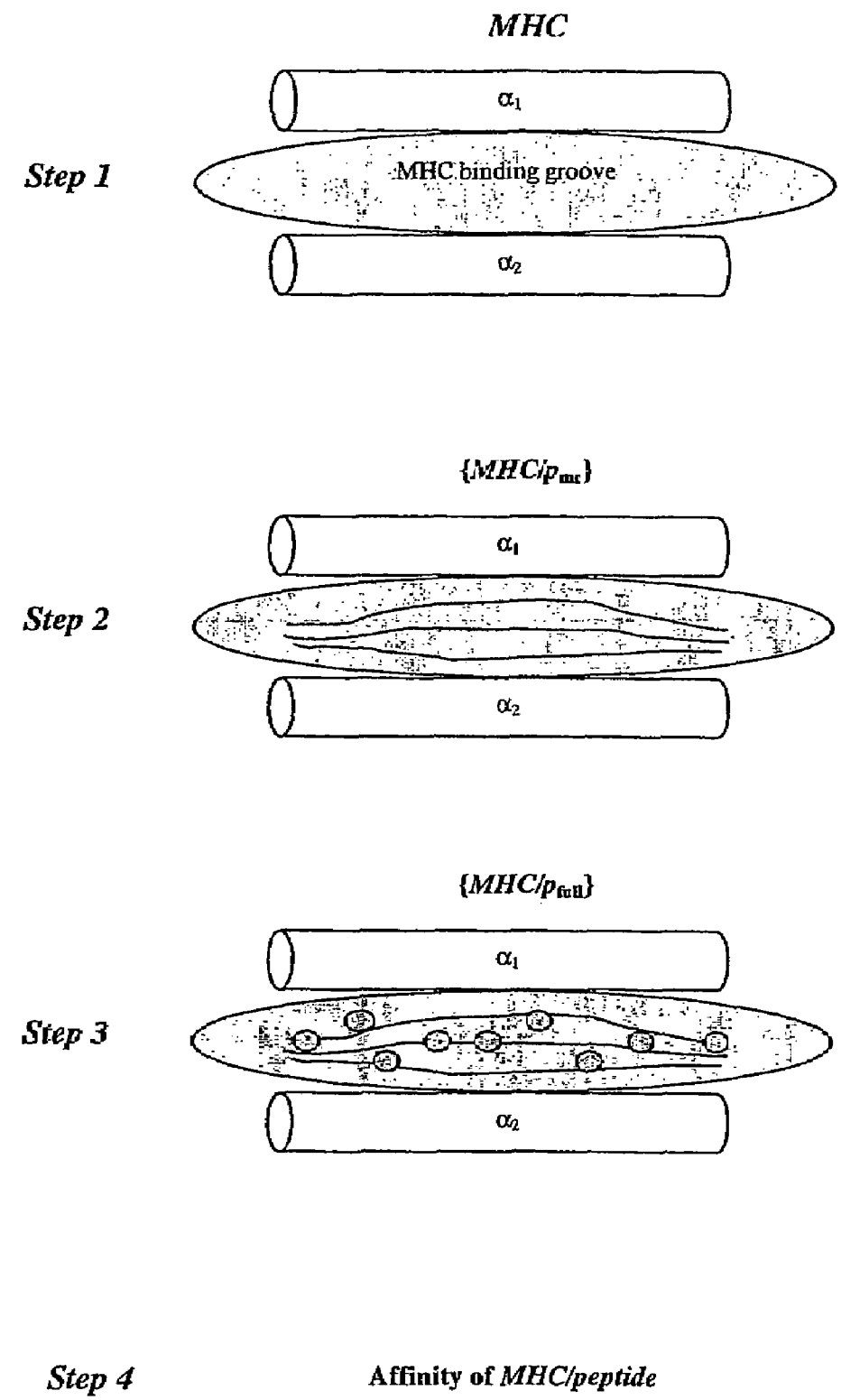
FIG. 1. Schematic overview of the information generated by steps 1-4 of a method of the present invention.
Figure 2:
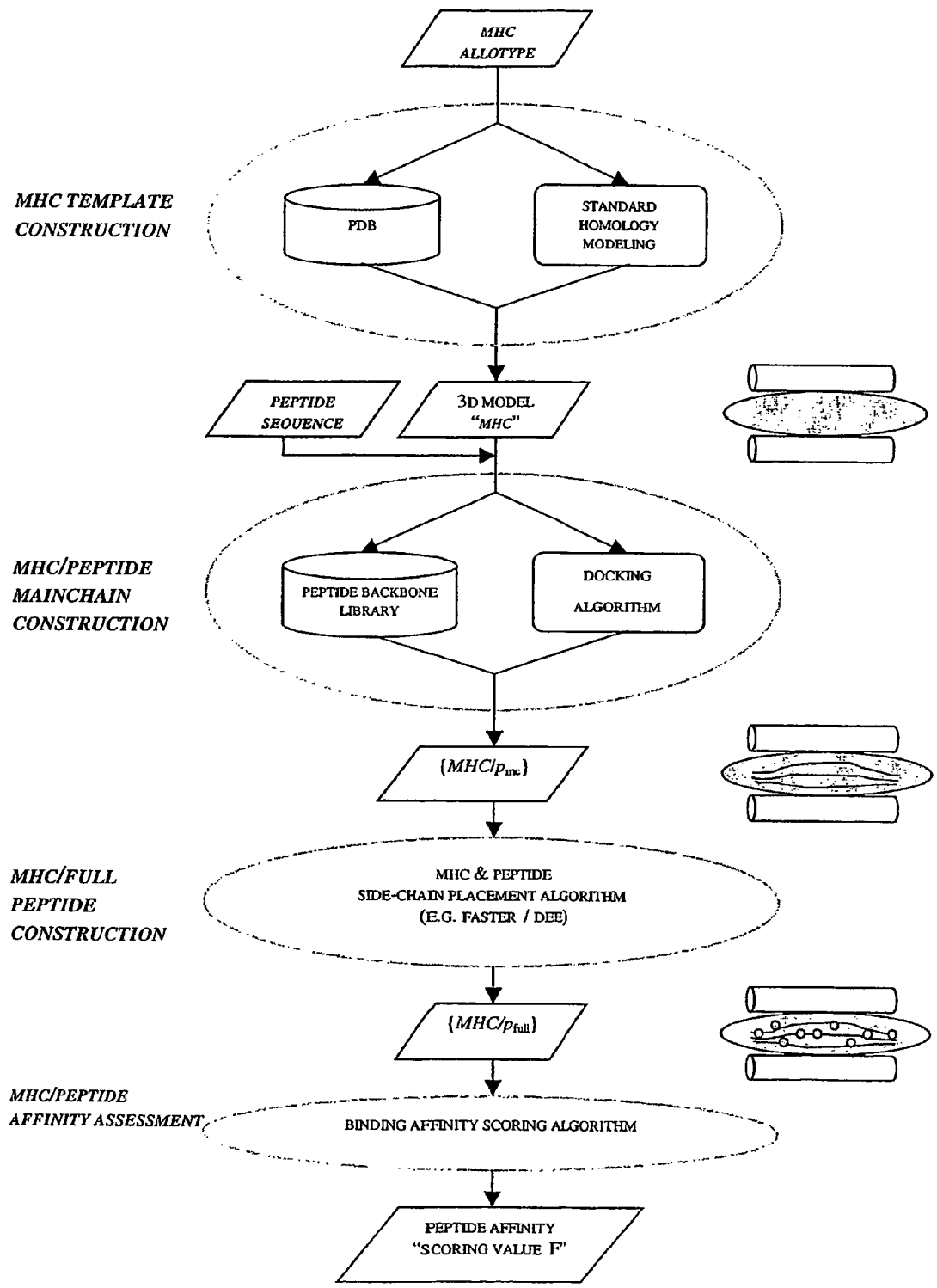
FIG. 2. Flow chart of a method of the present invention.

In the present example, we describe the flexible docking of the octapeptide VSV-8 (peptide p=RGYVYQGL) to murine MHC class I H-2K$^b$ (Fremont, D. H. et al., (1995) *Proc. Natl. Acad. Sci. USA* 92, 2479-2483). The following experimental conditions were used.

1. Peptide build-up: Tyr-P5 was chosen as the root residue because of its potential to form multiple contacts with the binding groove on the MHC. Elongation proceeded first towards the C- and then towards the N-terminal end, in the following manner: -Y->-YQ->-YQG->-YQGL>-VYQGL>-YVYQGL>-GYVYQGL>RGWYQGL.

2. Peptide translations: the peptide was systematically displaced to each of 79 translational offsets at relative distances of 1.0, 2.0 and 4.0 Å from the initial position.

3. Rotations: at each translational offset, discrete yet full-space rotation was performed over 84 rotational configurations.

4. Conformations: for the peptide residues Tyr-P3, Val-P4, Tyr-P5 and Gln-P6 the rotamer library contained 47 main-chain conformations; for Gly-P2 and Gly-P7 there were 125 rotamers and for the N- and C-terminal residues Arg-P1 and Leu-P8 there were 12.

5. Peptide and receptor side-chain conformations: side-chain conformations were retrieved from the backbone-dependent rotamer library described in Desmet et al. (1997). On average, there were 16 side-chain rotamers per residue. In addition to the 8 peptide residues, 28 receptor residues were assigned as flexible during the docking.

6. Force field: all-atom CHARMM force field comprising terms for bond stretching, bond angle bending, a periodic function for the torsion angles, a Lennard-Jones potential for the non-bonded atom pairs, a 10-12 potential for hydrogen bonds and a coulombic function for charged atoms. A distance-dependent dielectric constant was used ($\epsilon = r_{ij}$, where $r_{ij}$ is the distance between two atoms i and j; Warshel, A. and Levitt, M. (1976) *J. Mol. Biol.* 103, 227-249.

7. Water molecules: this experiment was performed in the presence of 9 crystallographically determined buried water molecules that were considered as part of the protein.

8. Partial-peptide conformations (fragments) were accepted for further elongation while using a relative energy threshold of 10 kcal mol$^{-1}$. In this experiment, final full-length peptides were accepted using the same threshold.

9. The docking algorithm terminated spontaneously and successfully after having elongated in a combinatorial fashion, i.e. residue by residue, all partial peptides to their full length.

The docking of the VSV-8 peptide to MHC class I H-2K$^b$ finally yielded a $\{MHC/p_{full}\}$ ensemble of 323 full-peptide configurations within an energy interval of 10 kcal mol$^{-1}$ (see TABLE 1). For this purpose, 1,117,957 partial peptide fragments had been processed during buildup.

TABLE 1

VSV-8 docking: Column 1: fragment length (number of residues); column 2: fragment sequence in one-letter code; column 3: total number of generated configurations for fragments of the corresponding length; column 4: number of accepted configurations; column 5: acceptance ratio in %; column 6: binding energy of the lowest-energy fragment (kcal mol$^{-1}$); column 6: incremental binding energy (kcal mol$^{-1}$).

| length | peptide | #conf | #accep | % accep | E__best | ΔE__best |
|---|---|---|---|---|---|---|
| 1 | ----Y--- | 311,892 | 920 | 0.29 | −24.4 | −24.4 |
| 2 | ----YQ-- | 43,240 | 2,074 | 4.80 | −43.8 | −19.4 |
| 3 | ----YQG- | 259,250 | 13,081 | 5.05 | −51.2 | −7.4 |
| 4 | ----YQGL | 156,972 | 289 | 0.18 | −73.9 | −22.7 |
| 5 | ---VYQGL | 13,583 | 1,064 | 7.83 | −82.0 | −8.1 |
| 6 | --YVYQGL | 50,008 | 1,148 | 2.30 | −109.5 | −27.5 |
| 7 | -GYVYQGL | 143,500 | 11,626 | 8.10 | −120.1 | −10.6 |
| 8 | RGYVYQGL | 139,512 | 323 | 0.23 | −147.1 | −27.0 |
| sum or average: | | 1,117,957 | 30,525 | 2.73 | | −18.4 |

Importantly, the docking algorithm rebuilds all side-chain conformations completely from scratch each time a partial or full peptide configuration is generated. In the present example this was accomplished by a dead-end elimination (DEE) method. In total, 1,117,957 separate DEE side-chain placement operations were performed, i.e. one for each peptide fragment. This approach might be described as an elegant way to decouple the side-chain modeling from the main-chain construction. It enormously reduces the space to be searched and yet avoids any potential bias from incorrectly positioned or frozen side-chains. As a possible alternative to the DEE method, the present inventors refer to the recently published FASTER method (Desmet et al., 2002). In general, any method for side-chain placement may be applicable. Prediction accuracy may actually form a lesser problem in view of the fact that the modeling of side-chains is repeated completely in step 3 of a method of the present invention. (But then only for the final full-length peptides, i.e. in the present example only 323 full structures instead of more than one million partial structures).

In summary, Table 1 shows that the acceptance ratio of partial peptide fragments was as low as 30,525 out of a total of 1,117,957 examined fragments or 2.73%. Higher acceptance ratios were observed when extending a fragment by a weakly restrained residue type, such as Gly at position P2. Yet, the combinatorial buildup did not lead to an explosion of fragments.

Figure 3:
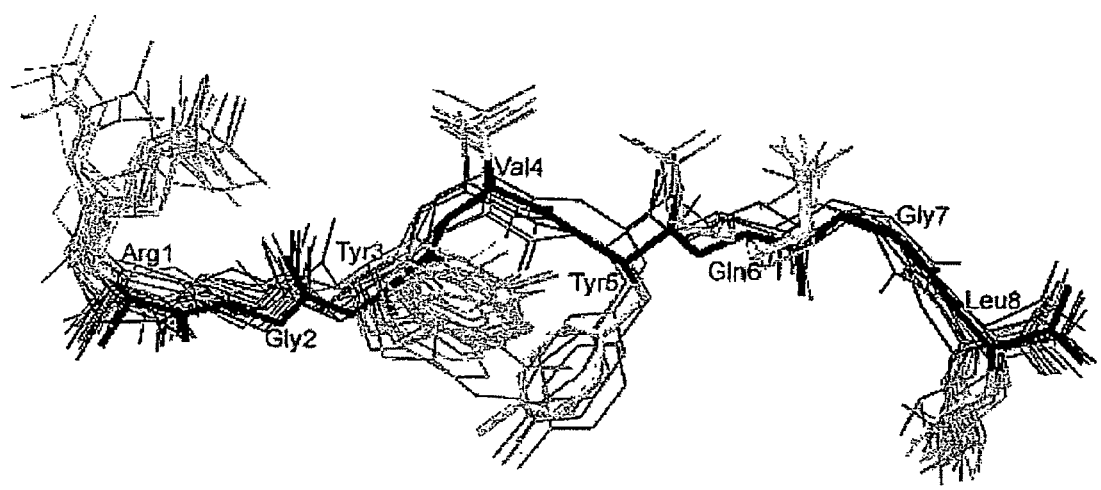
FIG. 3. Drawing of the 43 lowest energy peptides resulting from the VSV-8 docking. The crystallographically determined structure is presented by the sticks model. Black color is used for the main-chain atoms and gray for the side-chain atoms. Only "heavy" (non-H) atoms are shown. The viewpoint is from the "side" of the peptide with the N-terminus at the left. In the complex, the peptide is buried within the MHC $\alpha_1\alpha_2$ domain, with the $\alpha_2$-helix in front, the $\alpha_1$-helix at the back and the β-sheet at the bottom; the upper part of the peptide is solvent accessible. The MHC receptor itself, while present during docking, is not shown in the figure.

Of the 323 final structures within an energy interval of 10 kcal mol$^{-1}$, 43 had a binding energy within 5 kcal mol$^{-1}$ above the lowest (−147.1 kcal mol$^{-1}$) and are displayed in FIG. 3. Compared with the experimental structure of the complex, the lowest-energy peptide had a main-chain RMSD of only 0.56 Å. For the 43 displayed structures the average RMSD was 0.89±0.27 Å and for all 323 results it was 1.01±0.39 Å. The anchor residues Tyr-P3, Tyr-P5 and Leu-P8 were correctly packed into their complementary pockets (Fremont, D. H. et al., (1992) Science 257, 919-927). The side-chain of Leu-P8 adopted two different conformational states. Other apparently bi-stable conformations were observed for Gln-P6 and Arg-P1 (FIG. 3). The side-chain conformation of Gln-P6 was clearly coupled to the conformation of the MHC residues Glu-152 and Arg-155. Interestingly, the alternative conformation for these two residues has also been crystallographically observed, namely in the structure of the same H-2K$^b$ receptor complexed with the nonapeptide SEV-9 (Fremont et al., 1992). This illustrates the importance of taking into account at least some limited flexibility for the side-chains of the receptor.

Example 2

Systematic Docking of Viral Peptides

This example illustrates the performance of the docking algorithm described in EXAMPLE 1 in an application to large-scale docking. The purpose of this example is to demonstrate that the algorithm remains useful not only for studying selected cases that are known to form high-affinity complexes, but also for handling a large number of diverse peptides derived from a common protein source. Some features of such a collection are (i) that the set of peptides is not biased with respect to the presence of anchor residues and (ii) that the majority of peptides are most likely non-binders. Attention is paid to the computational requirements of the method, to statistics of the simulated structures and to potential difficulties in large-scale docking. This example also illustrates the preferred embodiment of steps 1 and 2 of a method of the present invention, i.e. MHC model preparation and flexible docking, respectively. In addition, we have performed a clustering analysis on the different observed peptide binding modes in order to study the (theoretical) variability of the main-chain of a peptide in a complex.

The test case was constructed as follows.

1. MHC receptor type/subtype: class I, A*0201
2. PDB structure for model preparation: 1DUZ a-chain
3. List of peptides to be docked: all nonameric (9-residue) peptides that can be derived from the human papillomavirus type 18 (HPV-18) E6 and E7 proteins, i.e. 150 and 97 peptides, respectively. Experimental binding affinities for the same set are available from the literature (Rudolf, M. P. et al., (2001) Clin. Cancer Res. 7, 788s-795s)
4. Docking conditions: force field and rotamer library are identical to Example 1. Translations were limited to 26 relative displacements over 0.5 Å from the original position. No rotational moves were allowed. All crystallographic water molecules were removed. The peptide residue P1 was selected as the root residue, thus elongation of fragments occurred from the N- to the C-terminus. The relative energy threshold for accepting partial peptide fragments was made dependent on the fragment length: 7, 7, 10, 13, 15, 15, 13 and 10 for lengths 1-9, respectively. This was necessary because partial peptides of intermediate length tended to form many tight but false interactions with the receptor (class I nonapeptides typically bulge out in the middle; Fremont et al., 1992).

Figure 4:
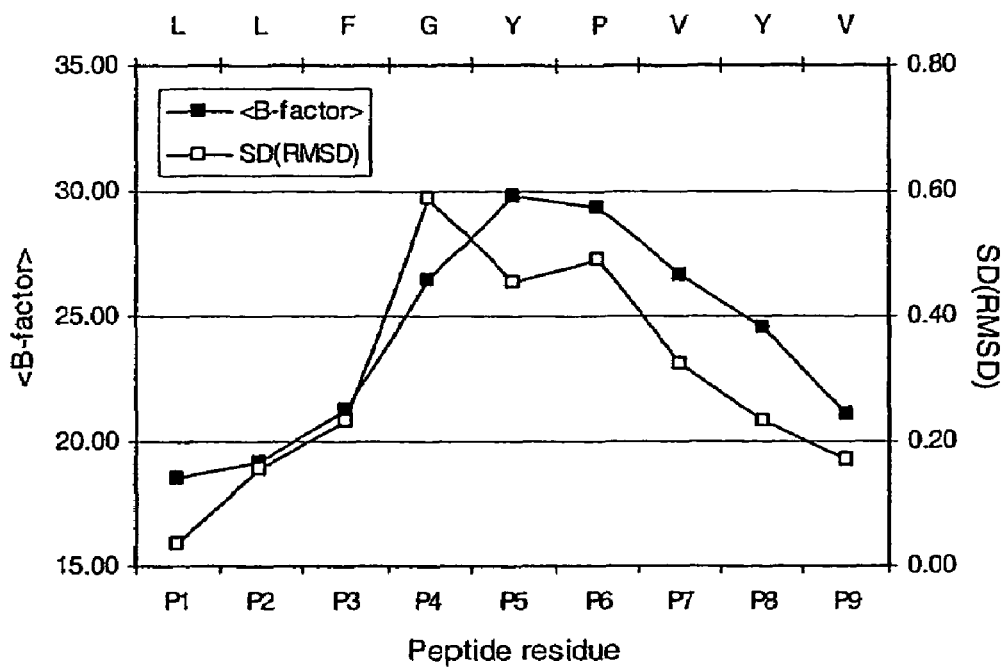
FIG. 4. Comparison between crystallographic temperature factors and theoretical structure variation. The average B-factors for the main-chain atoms of each residue of the peptide. LLFGYPVYV, obtained from the PDB entry 1DUZ (c-chain) are compared with the standard deviation on the main-chain RMSD, observed in the ensemble of docked structures. The docking experiment itself is described in EXAMPLE 2 of the present invention.

The selection of the PDB structure 1DUZ to construct the MHC template model was decided on basis of its high crystallographic resolution (1.8 Å). The whole PDB entry (chains a-e) were refined by 200 steps steepest descent energy minimization. Next, chains a (MHC) and c (peptide sequence LLFGYPVYV) were extracted. The only PDB information regarding the peptide that was retained upon docking were the coordinates of the backbone N, $C_\alpha$ and C atoms of residue P1. Prior to docking, each peptide was initialized by rebuilding it in an extended conformation with standard bond lengths and angles. The N, $C_\alpha$ and C atoms at residue P1 of the initialized peptide were fitted onto those observed in the PDB structure. Next, the peptide of the PDB file was removed. The MHC receptor together with the initialized peptide formed the starting situation for docking. A number of trial dockings were then performed using the "self" peptide LLFGYPVYV in order to determine the optimal settings for the relative energy thresholds of partial peptides of different length (values given supra, see: 4. Docking conditions). These trial experiments also served to reduce, in a safe way, the number of flexibly treated receptor side-chains: of the initial 29 side-chains in contact with the peptide, only 14 were finally kept flexible for they had a significant influence on the final ensemble of predicted structures (a7, a63, a66, a70, a73, a80, a84, a97, a99, a114, a116, a143, a146 and a159). With these settings, an ensemble of 210 structures was obtained for the A*0201/LLFGYPVYV complex. All peptide conformations compared well with the known crystallographic structure: the backbone RMSD ranged from 0.75 to 1.81 Å, with an average of 1.08±0.20 Å. A good correlation was observed between the crystallographic temperature factors and the structural variation exhibited by the ensemble of docked structures (FIG. 4). The B-factors, averaged over the main-chain atoms of each peptide residue, appeared to follow well the standard deviation on the main-chain RMSD with the crystallographic structure, abbreviated as SD(RMSD). The latter was taken as a measure of the theoretical flexibility of the peptide main-chain. A somewhat larger than expected flexibility was observed for Gly-P4, which was due to a high degree of torsional freedom of the peptide planes flanking P4. A surprisingly high flexibility was also observed for Pro-P6: the $C_\alpha\text{-}C_\beta$ vector of this residue displayed a relatively large rotational variation over ~90° around the peptide's principal axis. Yet, this theoretical result appears to be fully justified on basis of the experimental B-factors. Also, the general correlation between both parameters suggests that the computed ensemble reflects the real dynamic behavior of the bound peptide. Given these satisfactory results, it was concluded that the experimental settings were correctly chosen. The latter were applied in all next docking experiments.

Figure 5:
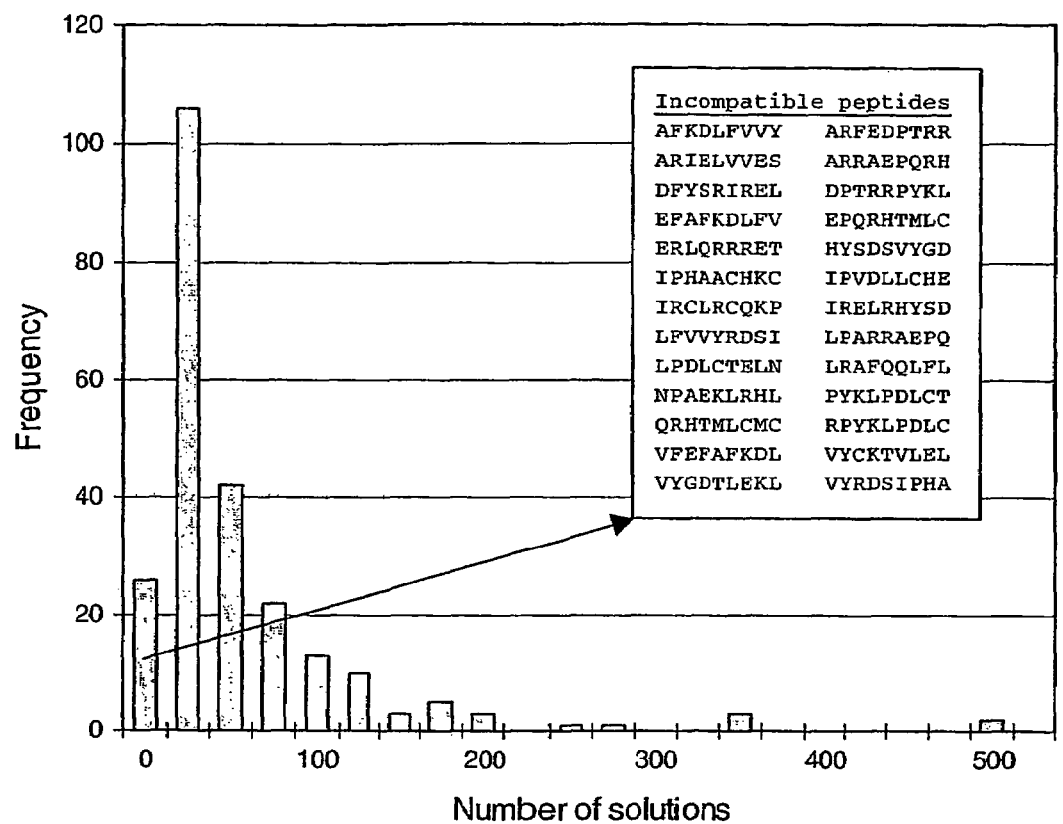
FIG. 5. Distribution of the number of docking solutions. All nonapeptides derived from the HPV E6 and E7 proteins were docked to the A*0201 receptor according to the protocol described in EXAMPLE 2 of the present invention. Each experiment yielded a set of receptor-compatible structures, ranging from 0 to 500. This diagram shows the distribution of docking solutions. 27 peptides were found to be incompatible with the receptor (inset). The main reason was the presence of either a bulky (R, Y, F) or a main-chain restricting (P) side-chain at position P2.

The large-scale docking of all HPV E6 and E7 peptides was performed in an automated fashion. The jobs were distributed over a cluster of four SGI Origin 200 computers, each equipped with four 270 MHz R12000 processors and 4 GB of memory. The average computational time needed per job was 8.7 CPU-hours, but some terminated almost immediately (0.01 CPU-h) or took a very long time (113.6 CPU-h). Typically, the docking of peptides containing large side-chains (Phe, Tyr, Arg) or Pro at position P2 tended to terminate before reaching their full length (FIG. 5). Analysis showed that the P2 residue of these peptides could be accommodated only in "non-standard" conformations, for sterical reasons.

Rudolf et al. (2001) published experimental affinity data for peptides derived from the HPV E6 and E7 sequences and binding to HLA A*0201. Fifteen out of the 247 displayed $IC_{50}$ values ranging from 3 to 943 nM. These peptides can thus be classified as strong or moderate binders to HLA A*0201. All other possible E6 and E7 peptides had $IC_{50}$ values higher than 1000 nM and can be termed weak or non-binders. Interestingly, many of the binding peptides had amino acid residues at positions P2 and P9 (the so-called primary anchor positions) that were non-typical for binding to HLA A*0201. For example, the top-ranked peptide, FAFKDLFVV (with Ala at position P2 instead of Leu, Ile or Met) displayed an $IC_{50}$ value of only 3 nM. The peptide FKDLFVVYR (with Lys at P2 and Arg at P9) being a very non-typical peptide, still had an $IC_{50}$ value of 500 nM. Two other binding peptides also had a non-typical aromatic residue at position P2, namely LYNLLIRCL and LFLNTLSFV. Especially for these peptides it was interesting to investigate the behavior of the docking algorithm.

It can be seen from FIG. 5 that none of the docking experiments failing to extend the peptide to its full length (26 out of 247 in total) concerned binding peptides (15 out of 247). Even the two binding peptides containing Tyr or Phe at position P2 could be successfully docked (the LYNLLIRCL and LFLNTLSFV docking resulted in 8 and 13 solutions, respectively), in contrast to many other peptides containing an aromatic side-chain at that position (FIG. 5). The FKDLFVVYR peptide could also be successfully docked (30 solutions) in spite of its bulky Arg side-chain at P9. In general, large side-chains at the primary anchors P2 and P9 had the effect of reducing the number of docking solutions due to sterical restraints. For some peptides, all of which are weak or non-binders, this led to premature termination of the docking process.

Another important observation was that the binding peptides had, on average, a much higher number of docking solutions than the non/weak binders. Binding peptides were represented by about twice as much solutions as non/weak binders (on average: 91 vs. 42 solutions, respectively). Similarly, only 3 of the 15 binders (20%) had less than 25 solutions whereas there were 132 of the 232 (57%) with less than 25 solutions among the non/weak binders. A logical conclusion is that the number of solutions obtained from the peptide docking experiments provides an indication of true conformational flexibility of a peptide within the MHC binding groove. This is consistent with the fundamental entropical principle stating that the higher the number of micro-states for a given macro-state (in this case the bound state) the higher will be the probability of that state. This example also illustrates the importance of working with ensembles of structures, rather than with a single modeled structure, to study the binding properties of MHC/peptide complexes.

Example 3

Construction of a Generic MHC/Peptide Database

An embodiment of the present invention is a method wherein the binding of one or more peptides is studied by applying an advanced database approach. As explained in the detailed description of the invention, such a database may be compiled from experimental (preferably X-ray) or theoretical (preferably docked) structures. A database obtained from known 3D structures has the advantage of being based on validated structural information but may suffer from the lack of such data, especially for certain MHC subtypes for which no complex structure has been solved. Even for well-represented subtypes, like the MHC class I HLA A*0201 allotype, there may be a strong bias towards particular observed peptide binding modes whereas many other feasible conformations are not yet represented in the Protein Databank. Consequently, in order to avoid problems related to a lack of experimental structures, the present inventors prefer to generate a database of MHC/P$_{mc}$ structures by systematically docking a large number of peptides of different sequence. Evidently, this can be done separately for different MHC subtypes and for peptides of different length. In this example we illustrate the construction of an {MHC/P$_{mc}$} ensemble for nonameric peptides oriented within the binding groove of HLA A*0201 (represented by PDB code 1DUZ, chain a).

The docking experiments were performed in an identical way to the experiments described in Example 2. A set of 180 nonameric peptide sequences to be docked was established in a pseudo-random fashion as follows. The present inventors have selected combinations of typical anchor residues at positions P2 and P9, i.e. Leu, Ile and Met at P2 and Leu, Ile and Val at P9. At all other positions, residue types were selected in a fully random fashion from the set of naturally occurring amino acids. This means that each of the 3×3=9 possible P2/P9 combinations was represented by 180/9=20 sequences with randomized residues at positions P1 and P3-P8. This procedure was followed to avoid the docking of peptides that cannot bind to the HLA A*0201 model because of incompatible anchor residues. At the same time, the randomization was assumed to generate sufficient variation in the peptide sequences to ensure a broad and unbiased sampling of the conformational space.

All but one docking experiments terminated in a successful way, i.e. only one simulation (of the peptide p=DIGVHKVV) terminated before the peptide was extended to its full length. All other simulations yielded a number of MHC/p$_{mc}$ solutions ranging from 1 to 500 (a user-set hard limit) and with an average of 22 per peptide. The total number of MHC/p$_{mc}$ structures was 3951.

All docking results were then pooled into one global {MHC/P$_{mc}$} ensemble, the side-chains were stripped off and the coordinates of the main-chain atoms of each peptide structure were stored in a suitable format in a database. This completed the construction of a generic database collection of MHC/P$_{mc}$ structures, applicable for studying the binding of nonapeptides to the MHC class I HLA A*0201 subtype.

Figure 6:
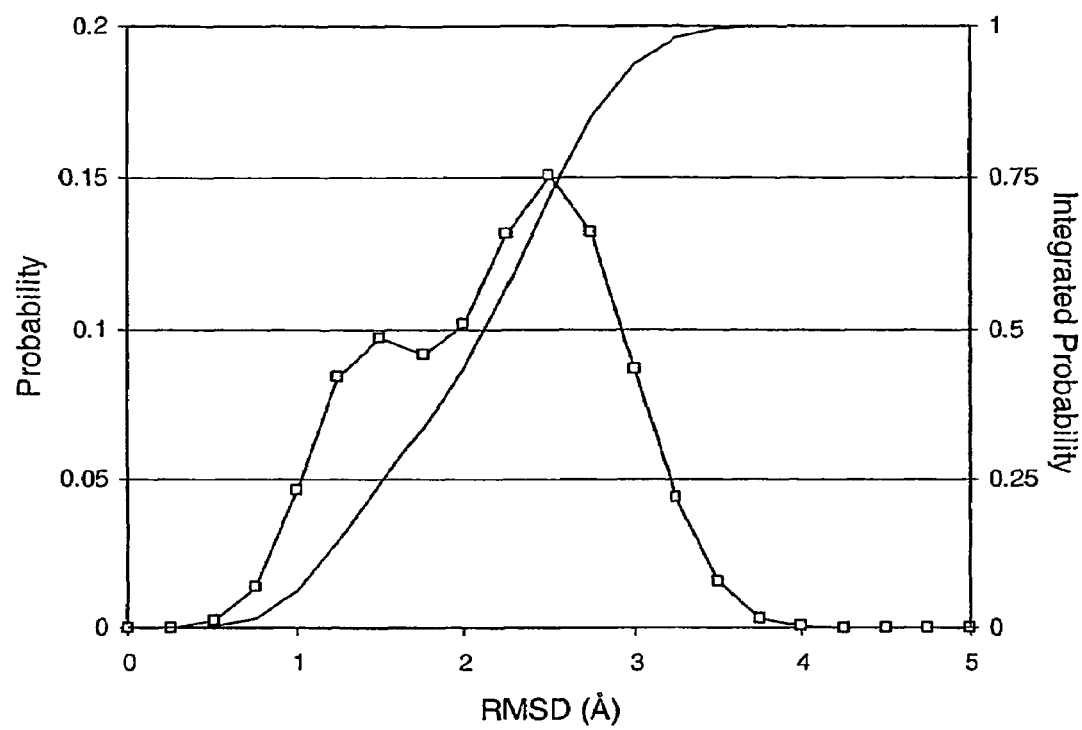
FIG. 6. Probability distribution of the root-mean-square deviation (RMSD) between the backbone atoms of any two peptide main-chain structures of the $\{MHC/P_{mc}\}$ ensemble described in EXAMPLE 3 of the present invention.

The ensemble was afterwards further analyzed with respect to the spatial distribution of peptide conformations in the {MHC/P$_{mc}$} ensemble. A suitable parameter to analyze this distribution is the peptide backbone root-mean-square deviation (RMSD) between different P$_{mc}$ structures in the ensemble. FIG. 6 shows the probability distribution of finding two main-chain structures having a certain RMSD. From the integrated probability curve it is seen that for any selected P$_{mc}$ structure the expected number of other structures with an RMSD≦0.5 Å is only about 0.3% of the total population. This shows that there is very limited, if any, redundancy among the members of the ensemble. The probability of an RMSD≦1 Å raises to 0.062 or 6.2%. With respect to modeling side-chains on backbones, a difference in RMSD of up to 1 Å can be expected to yield similar results. In other words, the further modeling of a peptide sequence onto each P$_{mc}$ structure will be statistically performed onto 0.062×3951 or about 250 relatively correct structures. This situation offers the possibility of a further clustering of the ensemble and/or the averaging of the results from different side-chain placements. Furthermore, the width of the probability distribution (~3 Å) suggests that a great variety of different binding modes, some of which may be required for specific peptides, are represented in the ensemble. From these results, the inventors concluded that the database approach forming an embodiment of the present invention may be very useful to predict the binding properties of a peptide within an MHC binding groove.

Example 4

Application of a Scoring Function to Predict Affinities

A property of an MHC/peptide complex is the affinity of the peptide for the MHC molecule. In accordance with the structure-based approach of the present invention, the binding affinity is predominantly derived from information related to the three-dimensional structure of a modeled complex. For this purpose, a so-called scoring function is required which translates structural information into one or more contributions that are expected to correlate with experimental affinity. Different contributions may be combined, for example added up, in order to provide a qualitative or quantitative score for an MHC/peptide complex of interest. By extension, different scores for different complexes may be computed, for example to rank different peptides according to their predicted affinity for a given MHC.

This example is included to illustrate a practical implementation of an embodiment of the present invention. This example is further included to demonstrate that the incorporation of an entropical contribution derived from an ensemble of modeled complex structures, rather than from a single modeled or experimental structure, significantly enhances the quality of predicted affinities. Said incorporation of an entropical component is in agreement with both Eqs. [1] and [5] of the present invention.

The results of the docking experiments described in example 2, more specifically the computer simulated binding of all HPV E6/E7 peptides to the HLA A*0201 receptor, have been further analyzed so as to eventually predict the affinity of the peptides. We recall that each of these docking experiments yielded an ensemble of MHC/p$_{mc}$ solutions, in accordance with a second step (MHC/peptide main-chain construction) of an embodiment of the present invention. These ensembles have been further processed in accordance with a third step (MHC/full peptide construction) and a fourth step (MHC/peptide affinity assessment) of an embodiment of the present invention.

First, the side-chains of each MHC/p$_{mc}$ structure in each ensemble were rebuilt by applying the DEE method of De Maeyer et al. (2000). Side-chains of the MHC receptor that were flexibly treated were the same as during the docking experiments described in Example 2 (14 in total). In order to reduce the effects from discrete rotameric placement of the side-chains, an additional modeling step was performed on each DEE-modeled structure: the full structures were further refined by 50 steps of steepest descent energy minimization to optimize local contacts. This resulted in the final set of ensembles {MHC/p$_{full}$} i.e. one ensemble of full complex structures for each peptide p. These data formed the major source of structure-related input information for a fourth step of an embodiment of the present invention.

Since complex formation involves a physico-chemical reaction between a receptor and ligand molecule from the unbound to the bound state, the binding process is driven by a change in free energy or ΔG (see Eqs. [3] and [4]). Consequently, an energetical evaluation of complex structures is preferably complemented by a similar evaluation of models of the unbound molecules. The free MHC receptor was therefore modeled separately by performing DEE side-chain placement with the same 14 flexibly treated side-chains as for the full complexes, followed by 50 steps of steepest descent energy minimization. Structures for the free peptide, on the other hand, were not generated by DEE modeling but by generating maximally extended conformations, also followed by 50 steps of steepest descent energy refinement. The binding energy $E_{bind}(p,i)$ of a solution i from the ensemble generated for a peptide p was calculated using equation [6]:

$$E_{bind}(p,i) = E_{complex}(p,i) - E_{MHC} - E_p(p) \quad [6]$$

where all energy values are the potential energies computed in accordance with the force field, and where $E_{complex}(p,i)$, $E_{MHC}$ and $E_p(p)$ are the potential energy of the complex, free receptor and free peptide, respectively. Next, the binding energies were averaged over all solutions i for each peptide p so as to obtain the average binding energy $<E_{bind}(p)>$ for the each ensemble $\{MHC/p_{full}\}$. This quantity corresponds to the term $<E>$ in Eq. [1] of the present invention.

Figure 7:
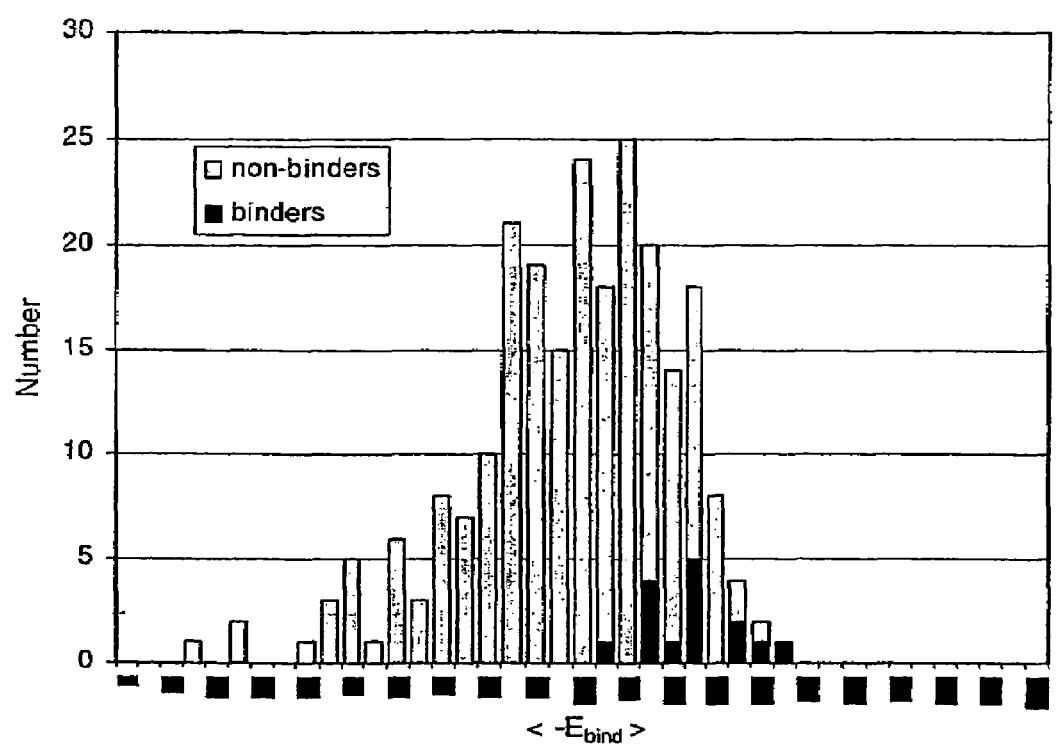
FIG. 7. Distribution of predicted average binding energies of HPV E6 and E7 peptides to HLA A*0201. Results are obtained as described in EXAMPLE 4 of the present invention. The energies do not include an entropical component.

FIG. 7 shows the distribution of the average binding energies for all predicted peptides. Peptides that were experimentally found to be good binders by Rudolf et al. (2001) are indicated in black whereas the non-binders are indicated with gray bars. It is clearly seen that the known binders tend to score well in comparison with the non-binders. Yet, both populations are not clearly separated in that several non-binders score better than most of the binders (they can be envisaged as "false positives"). This suggests that the discriminative power of potential energy alone is not strong enough to obtain good separation.

In view of the observation that most of the non-binding peptides had, on average, less $MHC/p_{mc}$ solutions in the docking step (see Example 2), it was investigated whether this factor could be converted into a significant, quantitative contribution of the scoring function. The most significant improvement in separation between binders and non-binders was obtained when adding to the potential energy term a logarithmic term depending on the total number of solutions N contained within each ensemble. Thus, the optimal scoring function F appeared to be of the form $$F(p) = <E_{bind}(p)> - c \times \ln N(p) \quad [7]$$

wherein c is a constant. Interestingly, the theory of statistical mechanics states that the entropy of (microcanonical) ensembles is logarithmically related to the number of microstates that are energetically accessible. (More specifically, the entropy S equals $k_B \ln(N)$ where $k_B$ is Boltzmann's constant). Thus, it was straightforward to rationalize the logarithmical dependence on the number of solutions as a true reflection the intrinsic conformational flexibility a peptide within a complex. In other words, the number of energetically feasible peptide conformations as derived from the simulations probably correlates in a statistically significant way with the true conformational entropy of a complex.

Figure 8:
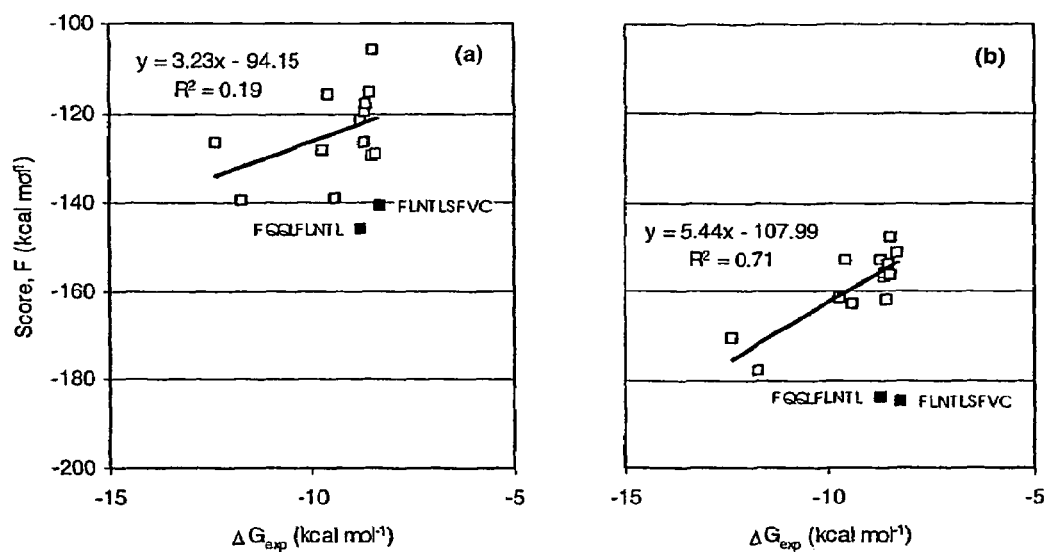
FIG. 8. Correlation between experimental and predicted affinities for 15 peptides from HPV E6 and E7 that are known to bind to HLA A*0201. Results are obtained as described in EXAMPLE 4 of the present invention. Panel (a), scores obtained from average binding energies only. Panel (b), scores obtained by including the entropical component. Two peptides (sequences indicated) were considered as outliers and their scores were not included in the regression analysis.

From the optimization of the separation of binders and non-binders, the best value for parameter c in Eq. [7] was found to be 20 kcal mol$^{-1}$. This value was applied in a further analysis wherein the predicted scores for the 15 binding peptides were directly correlated with the known experimental affinity (Rudolf et al. (2001) only published quantitative values for the binding peptides). FIG. 8 shows a correlation plot between predicted scores and known binding free energies. In FIG. 8a the entropical term is turned off (c=0) while in FIG. 8b it was set to its optimal value from the previous optimization procedure (c=20). Two peptides (FQQLFLNTL and FLNTLSFVC) showed an aberrant behavior compared to the rest and were considered as outliers. They were not included in the regression analysis. Interestingly, both peptides have a non-typical anchor residue (Gln at P2 of FQQLFLNTL and Cys at P9 of FLNTLSFVC ) while their scores appeared to be overestimated. This suggests that an additional correction factor may be desirable for typical anchor residues.

An important observation within the context of the present invention was the markedly better correlation obtained with the scoring function including the entropical term (panel b, $R^2=0.71$) compared to the function based exclusively on potential energy (panel a, $R^2=0.19$). Without the entropy component only a very weak correlation could be observed. This is consistent with the distribution plot presented in FIG. 7 showing that the energy component itself is practically useful only to identify peptides with a clear suboptimal energetic compatibility with the receptor. Only the combination of potential energy with a term reflecting conformational entropy enabled a good qualitative separation between binding and non-binding peptides. Furthermore, it enabled the establishing of a quantitative relationship between predicted and experimental affinities. FIG. 8b shows the equation that can be used to convert any score value F into a predicted free energy of binding.

We claim:

1. A method for predicting the binding affinity of a peptide for a major histocompatibility (MHC) class I or class II molecule, the method being executed on a computer under the control of a program stored on the computer, comprising the following steps:
   a) receiving a representation of a complete or partial three-dimensional structure of a MHC class I or class II molecule,
   b) obtaining an ensemble of conformational representations of peptide backbone structures of said peptide, said conformational representations located within the binding site of said MHC molecule,
   c) modeling the side-chains of said peptide for each peptide backbone structure of said ensemble in relation to said MHC molecule, thereby obtaining an ensemble of modeled MHC/peptide complexes,
   d) evaluating the binding properties of said peptide for said MHC molecule, by using scoring function which combines at least:
      d1) average binding energy component obtained by evaluating one or more components of the potential energy of each complex of the ensemble of step c),
      d2) conformational entropy component obtained by evaluating the conformational entropy for the complete ensemble of modeled MHC/peptide complexes of step c), and
   e) outputting said evaluation to a user in a user-readable format.

2. A method according to claim 1 wherein said representation of step (a) is obtained from one of the following:
   one or more experimentally determined structures obtained by for example X-ray crystallography, nuclear magnetic resonance spectroscopy, scanning microscopy, or
   one or more models derived from an experimentally determined structure, whereby said experimentally determined structure has a high sequence identity to said MHC molecule.

3. A method according to claim 1 wherein said conformational representation of step (b) is generated by a computer modeling method, said method being able to generate multiple energetically favorable backbone configurations in relation to said MHC molecule.

4. A method according to claim 1 wherein said conformational representation of step (b) is retrieved from a library of peptide structures pre-oriented in relation to said MHC molecule.

5. A method according to claim 1 wherein a complex within said ensemble of step (c) is obtained from a side-chain placement algorithm.

6. A method according to claim 5 wherein the side-chain placement of step (c) not only involves placing the side-chains of the peptide itself, but also involves placing at least one side-chain of said MHC molecule that are in contact with said peptide.

7. A method according to claim 5 wherein a complex within said ensemble of step (c) is obtained from a side-chain placement algorithm suited for global side-chain optimization.

8. A method according to claim 5 wherein the side-chain placement algorithm is a dead-end elimination (DEE) algorithm, characterized in that said DEE algorithm eliminates rotameric conformations on the basis of a mathematical criterion that allows the detection of conformations that are not compatible with the globally optimal conformation.

9. A method according to claim 5 wherein the side-chain placement algorithm is a FASTER algorithm, said algorithm being characterized by a repeated perturbation, relaxation and evaluation step.

10. A method according to claim 1 wherein the binding affinity of step (d) is represented by a single scoring value for the whole ensemble of MHC/peptide complexes, said scoring value comprising the sum of the conformational entropy for the complete ensemble of MHC/peptide complexes, and the average of the said energetical components of each of the complexes of said ensemble.

11. A method according to claim 1 wherein the binding affinity of step (d) is evaluated for the global complex, thereby accounting for interactions between pairs of residues from the peptide, the MHC molecule and both the peptide and the MHC molecule.

12. A method according to claim 1 wherein the entropical component reflects the overall conformational flexibility of the peptide.

13. A method according to claim 1 wherein the conformational representations of said peptide contained in said library are derived from experimentally determined structures.

14. A method according to claim 1 wherein the conformational representations of said peptide contained in said library are derived from computer-generated structures.

15. A method according to claim 1 wherein said peptide comprises one or more non-naturally occurring amino acids.

16. A method according to claim 1 wherein said MHC class I molecule comprises an HLA antigen selected from any of the HLA-A, HLA-B, HLA-C, HLA-E, HLA-F and HLA-G alleles.

17. A method according to claim 1 wherein said MHC class II molecule comprises an HLA antigen selected from any of the HLA-DR, HLA-DQ and HLA-DP gene products.

* * * * *